US010413270B2

(12) United States Patent
Noda et al.

(10) Patent No.: US 10,413,270 B2
(45) Date of Patent: Sep. 17, 2019

(54) MEDICAL IMAGE DIAGNOSTIC APPARATUS

(71) Applicant: Toshiba Medical Systems Corporation, Otawara-shi, Tochigi (JP)

(72) Inventors: Koji Noda, Nasushiobara (JP);
Tsuyoshi Kojima, Nasushiobara (JP);
Toshio Muroi, Nasushiobara (JP);
Shinji Nishizawa, Nasushiobara (JP);
Yoshihito Abe, Utsunomiya (JP);
Junko Shibata, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 119 days.

(21) Appl. No.: 15/812,074

(22) Filed: Nov. 14, 2017

(65) Prior Publication Data
US 2018/0132814 A1 May 17, 2018

(30) Foreign Application Priority Data

Nov. 15, 2016 (JP) .................................. 2016-222507
Nov. 10, 2017 (JP) .................................. 2017-217021

(51) Int. Cl.
*A61B 6/00* (2006.01)
*A61B 6/03* (2006.01)

(52) U.S. Cl.
CPC .............. *A61B 6/586* (2013.01); *A61B 6/032* (2013.01); *A61B 6/035* (2013.01); *A61B 6/4441* (2013.01); *A61B 6/4476* (2013.01); *A61B 6/465* (2013.01); *A61B 6/487* (2013.01); *A61B 6/54* (2013.01); *A61B 6/547* (2013.01); *A61B 6/581* (2013.01); *A61B 6/467* (2013.01)

(58) Field of Classification Search
None
See application file for complete search history.

(56) References Cited

U.S. PATENT DOCUMENTS

| 2010/0119043 | A1* | 5/2010 | Yakubovsky | .......... | A61B 6/032 378/98.5 |
| 2012/0053733 | A1* | 3/2012 | Kani | ................ | G01N 23/20016 700/275 |
| 2015/0142377 | A1* | 5/2015 | Kishida | .................... | G01B 7/30 702/151 |

FOREIGN PATENT DOCUMENTS

| JP | 08-170824 | 7/1996 |
| JP | 09-097285 | 4/1997 |
| JP | 2001-185599 | 7/2001 |
| JP | 2002-366023 | 12/2002 |
| JP | 2007-117464 | 5/2007 |

(Continued)

*Primary Examiner* — Hoon K Song
(74) *Attorney, Agent, or Firm* — Oblon, McClelland, Maier & Neustadt, L.L.P.

(57) ABSTRACT

According to one embodiment, a medical image diagnostic apparatus includes a holding device, a driving unit, a first encoder, a second encoder, and processing circuitry. The holding device holds an X-ray generator and an X-ray detector such that the X-ray generator and the X-ray detector are rotatable. The driving unit transmits a rotating force of a driving motor to a rotation axis through a power transmission mechanism. The first encoder detects a rotation of the driving motor. The second encoder detects a rotation of the rotation axis. The processing circuitry detects an abnormal state of the power transmission mechanism, based on a time difference between a first pulse output from the first encoder and a corresponding second pulse output from the second encoder.

17 Claims, 15 Drawing Sheets

(56) References Cited

FOREIGN PATENT DOCUMENTS

| | | |
|---|---|---|
| JP | 2008-174336 | 7/2008 |
| JP | 2010-240157 | 10/2010 |
| JP | 2011-036477 | 2/2011 |
| JP | 2015-185021 | 10/2015 |
| WO | 2015/146295 | 10/2015 |

\* cited by examiner

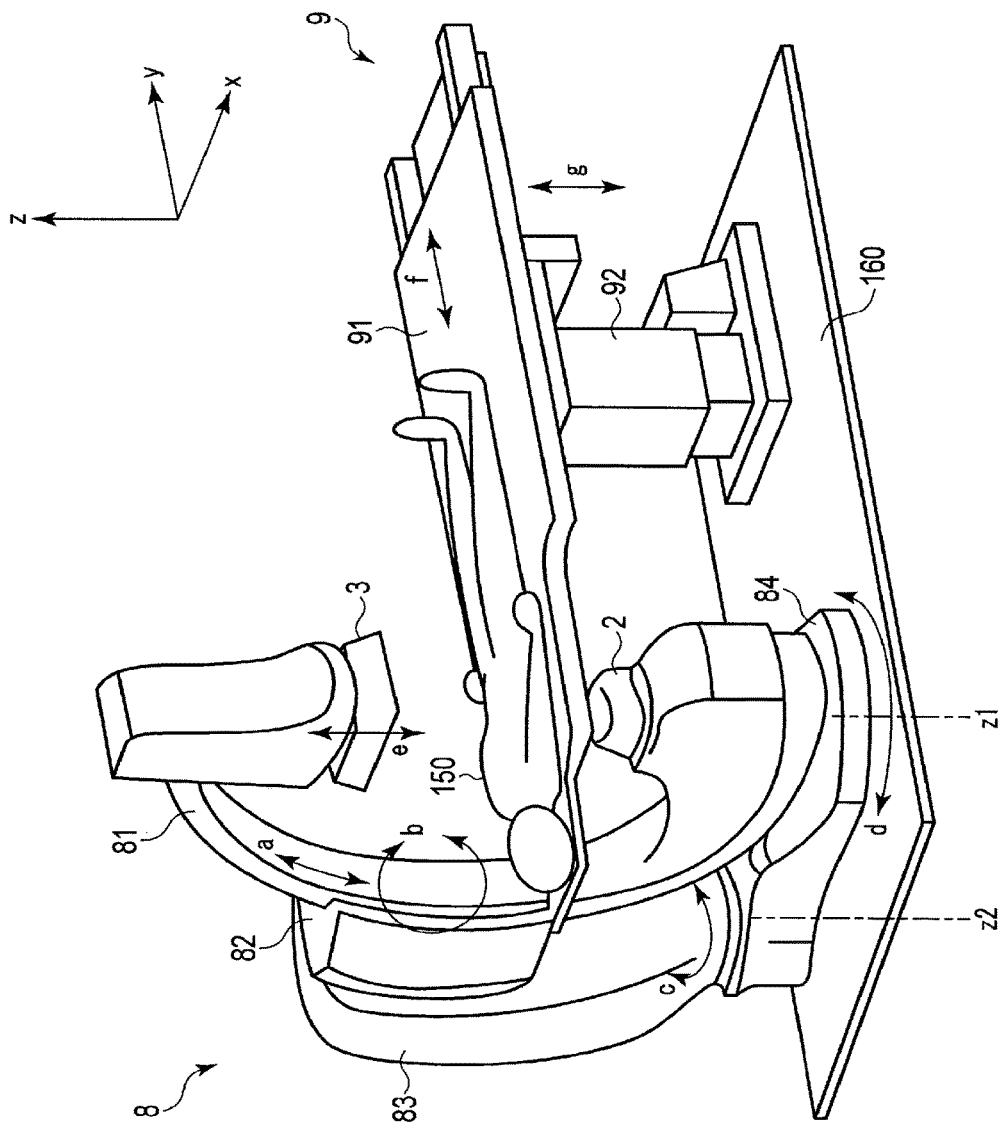
F I G. 2

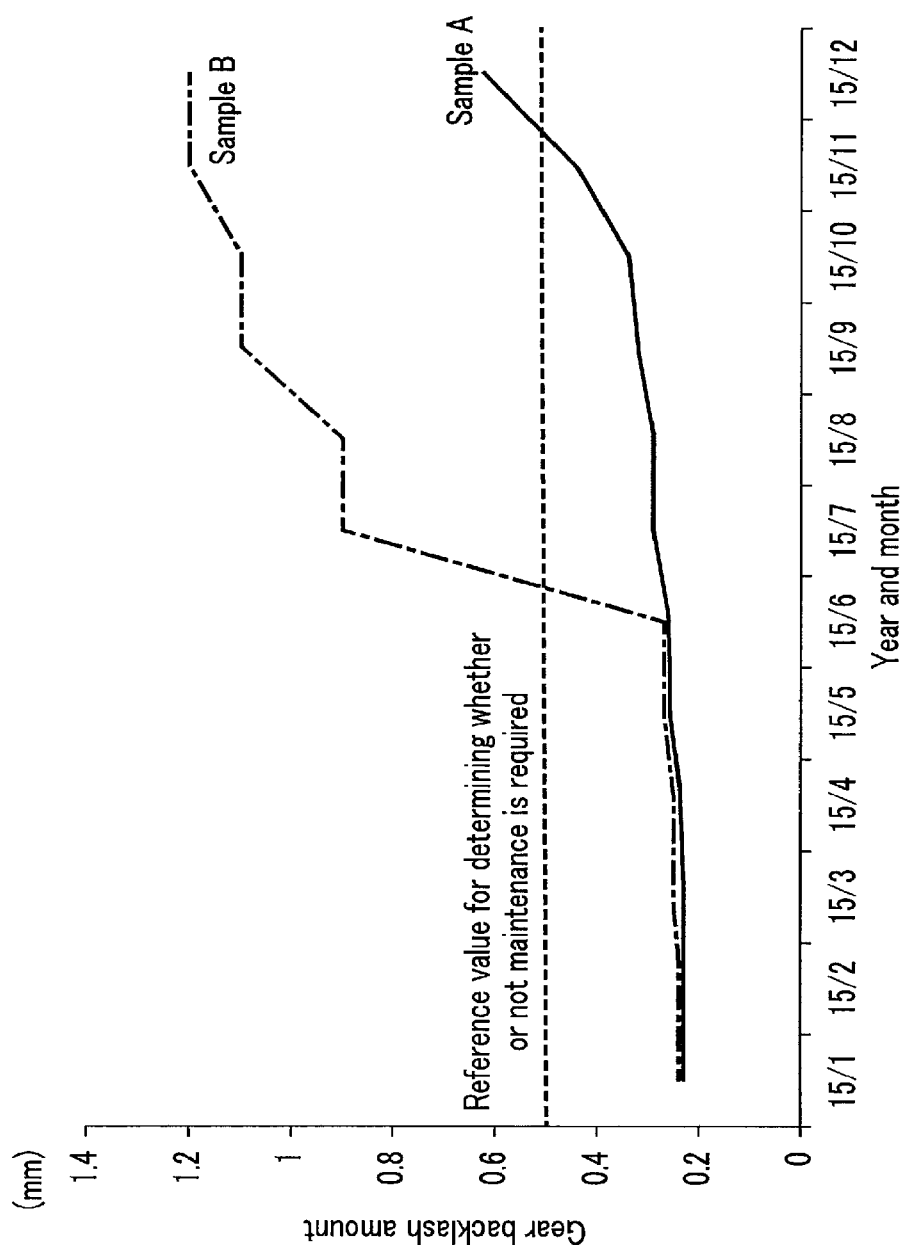
F I G. 5

| Function | Secular change (sample A) | Sudden event (collision/overload) (sample B) | Remarks |
|---|---|---|---|
| Rotation DSA imaging | ○ | × | ×: execution is restricted |
| 3D-DSA imaging | ○ | × | ×: execution is restricted |
| 3D-LCI imaging | × | × | ×: execution is restricted |
| Operating speed | ○ | × | ×: fallback operation is performed at low speed |
| Operating range (full-stroke operation) | ○ | × | ×: operation is enabled only within the range determined in gravitation direction at the time of error occurrence |
| Acceleration/deceleration control parameters | ○ | × | ×: fallback operation is performed for lengthened acceleration/deceleration time |

○: execution is enabled with no restriction
×: execution is restricted or fallback operation

F I G. 12

| Driving system | Secular change (sample A) | Sudden event (collision/overload) (sample B) | Remarks |
|---|---|---|---|
| Main rotation | ○ | × | ×: operation is restricted and necessity for maintenance is displayed |
| C-arm slide | ○ | × | ×: operation is restricted and necessity for maintenance is displayed |
| Mechanism for moving detector forward or backward | ○ | × | ×: operation is restricted and necessity for maintenance is displayed |

○: ordinary operation is enabled with no restriction
×: execution is restricted or fallback operation

F I G. 13

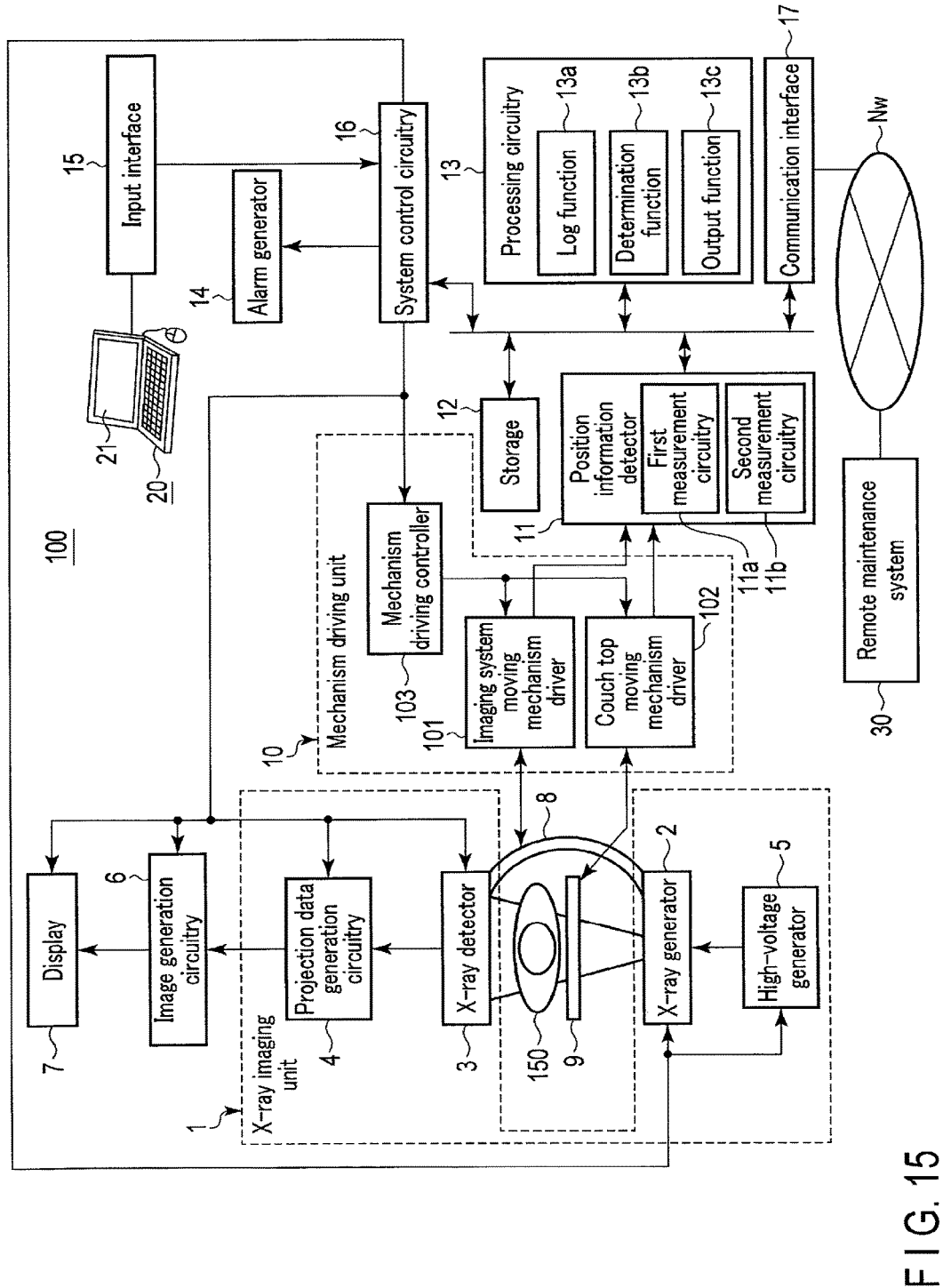
F I G. 15

| Time | Operation event | Operation axis | Normalization value (internal encoder) | Normalization value (load encoder) | Difference value of normalization values | Pulse number (raw value) of internal encoder | Pulse number (raw value) of load encoder | Difference value of pulse numbers | Completion of service adjustment | Down mode | Operation | Motor output log |
|------|-----------------|----------------|----------------------------------------|-----------------------------------|-----------------------------------------|---------------------------------------------|-----------------------------------------|----------------------------------|------------------------------|-----------|-----------|-----------------|
|      |                 |                |                                        |                                   |                                         |                                             |                                         |                                  |                              |           |           |                 |
|      |                 |                |                                        |                                   |                                         |                                             |                                         |                                  |                              |           |           |                 |
|      |                 |                |                                        |                                   |                                         |                                             |                                         |                                  |                              |           |           |                 |
|      |                 |                |                                        |                                   |                                         |                                             |                                         |                                  |                              |           |           |                 |

F I G. 16

MEDICAL IMAGE DIAGNOSTIC APPARATUS

CROSS-REFERENCE TO RELATED APPLICATIONS

This application is based upon and claims the benefit of priority from prior Japanese Patent Applications No. 2016-222507, filed on Nov. 15, 2016, and No. 2017-217021, filed on Nov. 10, 2017, the entire contents of all of which are incorporated herein by reference.

FIELD

Embodiments described herein relate generally to a medical image diagnostic apparatus.

BACKGROUND

In general, a medical image diagnostic apparatus is provided with a driving system for moving or rotating a holding device, which holds an X-ray generator and an X-ray detector, in a predetermined direction, so that X-ray imaging can be performed for a subject from a desired position or in a desired direction. The driving system includes a rotation mechanism which enables the rotating force of a driving motor to be transmitted to a rotation axis through a power transmission mechanism including a belt, a gear, a chain, etc.

This type of driving system detects an error, such as a predetermined amount of positional shift or an uncontrollable condition, based on the difference between the rotating speed of the driving motor and the theoretical value of the rotating speed of the load-side rotation axis, and informs the operator of the occurrence of the error by error indication. In this case, the rotation axis cannot be driven, and the examination or medical treatment stops. When the cause of the error is eliminated thereafter, the rotation axis can be driven again, and the next examination can be performed.

Even if the error indication is not performed, the power transmission mechanism may include a loosened portion, or a portion that undergoes a backlash in a gap or the like. In such a case, the tracking performance of the motor operation may deteriorate, and the positioning operation by the rotation axis may not be performed properly. Therefore, the driving system is maintained regularly without reference to the condition of the apparatus and the frequency of use. In the maintenance operation, the cover is removed from the apparatus, and the portions of the power transmission mechanism are visually checked to see whether there is a loosened portion or a portion that undergoes a backlash, and if such a portion is found, proper adjustment is made.

The medical image diagnostic apparatus mentioned above does not cause any particular problems during normal use. However, since the maintenance is performed regularly even if the apparatus is in a good condition or is not used frequently, the operation rate of the apparatus may decrease.

An object is to prevent a decrease in the operation rate without reference to the regular maintenance operation.

BRIEF DESCRIPTION OF THE DRAWINGS

FIG. 2 is a perspective view showing a configuration of the medical image diagnostic apparatus of the embodiment.

FIG. 5 is a schematic diagram showing how a gear backlash amount changes with time in the embodiment and how it changes after the occurrence of a sudden event.

FIG. 12 is a schematic diagram illustrating the control function of a medical image diagnostic apparatus according to a fourth embodiment.

FIG. 13 is a schematic diagram illustrating how a driving system operates in the embodiment.

FIG. 15 is a schematic diagram showing a configuration of a medical image diagnostic apparatus according to a fifth embodiment, together with the neighboring configuration.

FIG. 16 is a schematic diagram illustrating log information used in the embodiment.

DETAILED DESCRIPTION

In general, according to one embodiment, a medical image diagnostic apparatus includes a holding device, a driving unit, a first encoder, a second encoder and processing circuitry.

The holding device is configured to hold an X-ray generator and an X-ray detector such that the X-ray generator and the X-ray detector are rotatable around a rotation axis.

The driving unit includes a driving motor and a power transmission mechanism. The driving unit is configured to transmit a rotating force of the driving motor to the rotation axis through the power transmission mechanism so as to rotate the holding device.

The first encoder is configured to detect a rotation of the driving motor.

The second encoder is configured to detect a rotation of the rotation axis.

The processing circuitry is configured to detect an abnormal state of the power transmission mechanism, based on a time difference between a first pulse of a first pulse signal output from the first encoder and a corresponding second pulse of a second pulse signal output from the second encoder.

Since the "time difference" corresponds to the "difference in pulse number", the "time difference" recited in the claims encompasses the "difference in pulse number."

To supplement this, the difference between the pulse number of the first pulse signal within a predetermined operating range and the pulse number of the second pulse signal within the same operating range may be used as the time difference between the first pulse and the second pulse. For example, time difference "zero" may be detected as difference "zero" between the pulse number corresponding to 10 degrees/sec of the first pulse signal and the pulse number corresponding to 10 degrees/sec of the second pulse signal. Where the time difference is not zero, the difference between the pulse number of the first pulse signal in one second and the pulse number of the second pulse signal in one second is not zero.

A description will now be given of embodiments with reference to the accompanying drawings. In connection with the embodiments set forth below, reference will be made to a medical image diagnostic apparatus for cardiovascular diagnosis wherein the holding unit is a C arm to the ends of which an X-ray generator and an X-ray detector (imaging system) are attached. However, the embodiments are not limited to this. For example, the holding unit may be a C arm or Ω arm hanging from the ceiling. In addition, the medical image diagnostic apparatus may be a general-purpose type that can be used for both cardiovascular diagnosis and digestive diagnosis. The "medical image diagnostic apparatus" may be read as an "X-ray diagnostic apparatus."

First Embodiment

Figure 1:
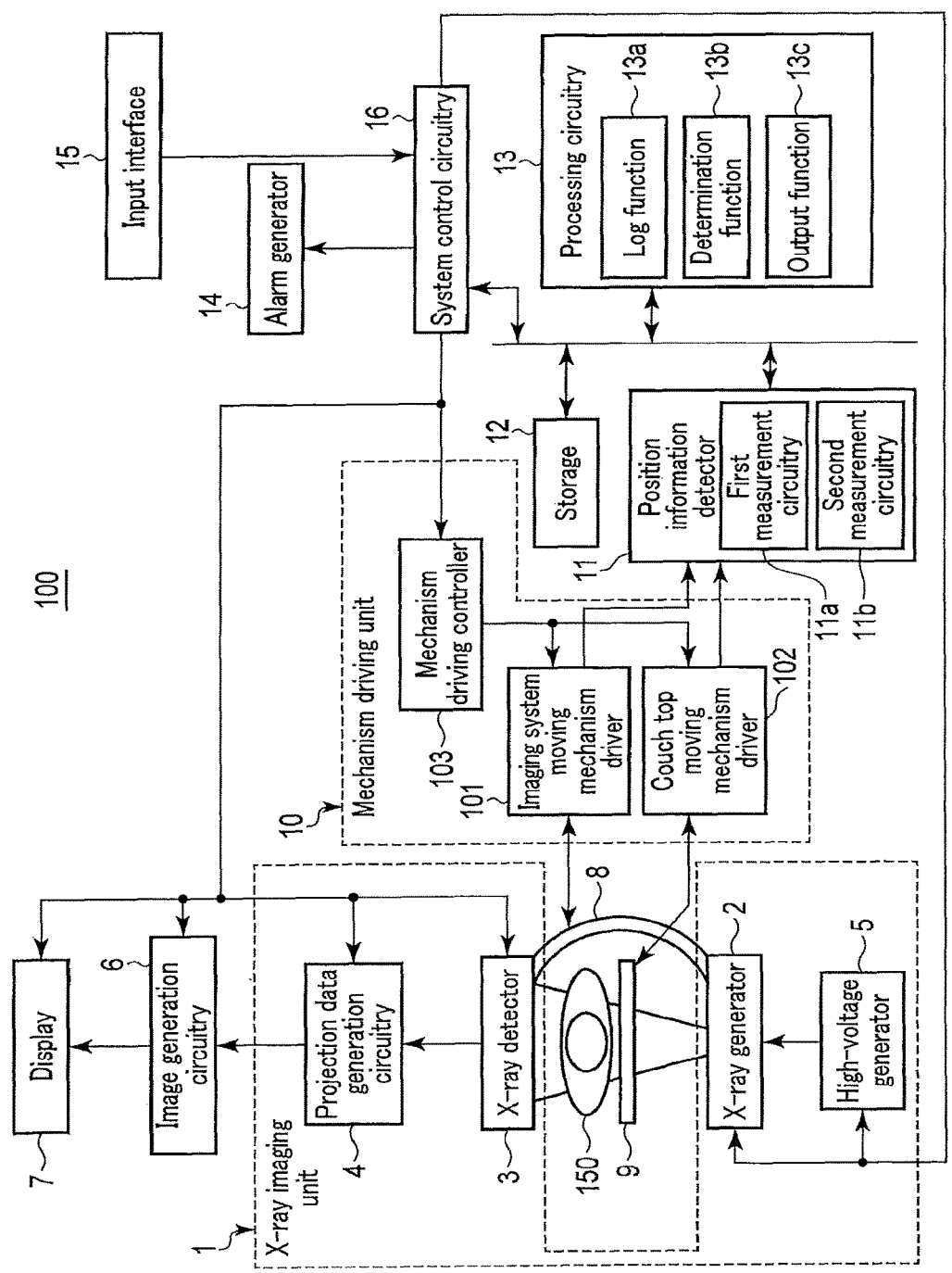
FIG. 1 is a schematic diagram showing a configuration of a medical image diagnostic apparatus according to a first embodiment.
Figure 3:
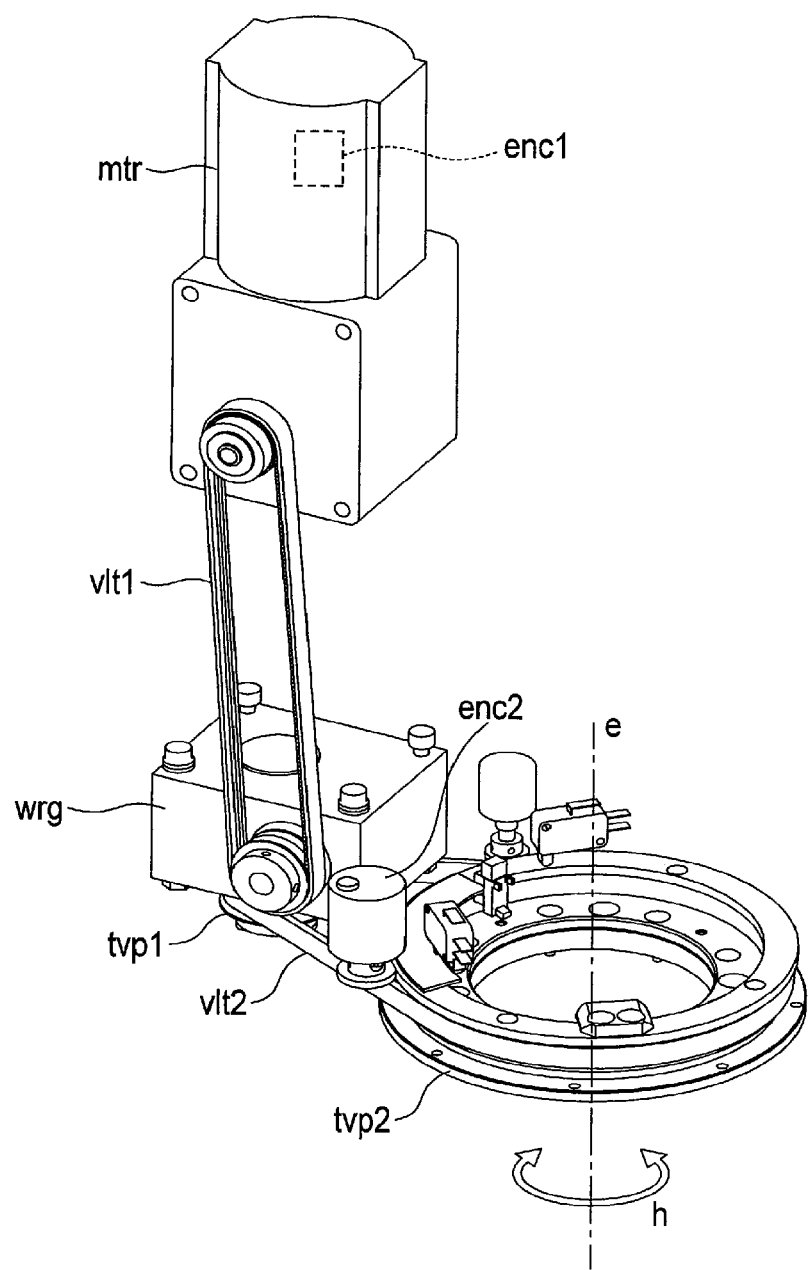
FIG. 3 is a schematic diagram showing a configuration example of a driving system of the embodiment.

FIG. 1 and FIG. 2 are a schematic view and a perspective view showing the configuration of a medical image diagnostic apparatus according to the first embodiment. FIG. 3 is a schematic view showing a configuration example of the driving system used in the first embodiment. The medical image diagnostic apparatus 100 comprises: an X-ray imaging unit 1 which generates projection data by emitting an X-ray toward a subject 150 and detecting the X-ray passing through the subject 150; image generation circuitry 6 which generates image data based on the projection data; a display 7 which displays the generated image data; a holding device 8 provided with a holding unit which holds the X-ray generator 2 and X-ray detector 3 (imaging system) of the X-ray imaging unit 1 and moves or rotates the X-ray generator 2 and X-ray detector 3 around the subject 150 in a predetermined direction; and a couch 9 which moves a couch top in a predetermined direction, with the subject 150 placed on the couch top.

The medical image diagnostic apparatus 100 also comprise: a mechanism driving unit 10 which supplies a driving signal to the driving mechanisms of the holding device 8 and the couch 9; a position information detector 11 which detects position information on the holding unit and the imaging system attached to the holding unit and which also detects position information on the touch top of the couch 9; storage 12; processing circuitry 13; an alarm generator 14; an input interface 15 which inputs subject information, determines X-ray imaging conditions including X-ray irradiation conditions, and inputs various command signals; and system control circuitry 16 which integratedly controls the above-mentioned units and enables safe and efficient X-ray imaging to be performed for the subject 150.

The X-ray imaging unit 1 comprises an X-ray generator 2, an X-ray detector 3, projection data generation circuitry 4 and a high-voltage generator 5, and has the function of generating projection data based on the amount of X-ray transmitted through the subject 150.

The X-ray generator 2 generates X-rays to be radiated to the subject 150 placed on the couch top 91. The X-ray generator 2 comprises an X-ray tube and an X-ray collimator which forms an X-ray corn beam from the X-rays emitted from the X-ray tube. The X-ray tube is a vacuum tube for generating X-rays. The X-ray tube generates X-rays by accelerating electrons discharged from a cathode (filament) by application of a high voltage and bombarding them against a tungsten anode. The X-ray collimator is located between the X-ray tube and the subject 150 and collimates the X-ray beam coming from the X-ray tube such that the X-ray beam has a size corresponding to a predetermined irradiation field.

The X-ray detector 3 detects the X-rays transmitted through the subject 150. The X-ray detector 3 may be either a detector which converts the X-rays directly into electric charges, or a detector which first converts the X-rays into light and then converts the light into electric charges. Although the former type of detector will be mentioned below, the X-ray detector 3 may be the latter type. The X-ray detector 3 of the present embodiment comprises a planar detector which converts the X-rays transmitted through the subject 150 into electric charges and accumulates the electric charges, and a gate driver which generates a driving pulse for reading the electric charges accumulated in the planar detector.

The planar detector comprises tiny detection elements arranged in two dimensions. Each of the detection elements includes a photoelectric conversion layer which senses X-rays and generates electric charges in accordance with the amount of incident X-rays, a charge accumulation capacitor which accumulates the charges generated by the photoelectric conversion layer, and a thin film transistor (TFT) which reads the electric charges accumulated in the charge accumulation capacitor at predetermined times (none of these are shown in the drawings). The accumulated electric charges are sequentially read with a driving pulse supplied from the gate driver.

The projection data generation circuitry 4 comprises a charge-voltage converter which converts electric charges, read from the planar detector in parallel in units of rows or columns, into a voltage, an analog-digital converter which converts an output of the charge-voltage converter into a digital signal, and a parallel-serial converter which converts digital parallel signals into time-series serial signals.

The high-voltage generator 5 comprises a high-voltage generation unit which generates a high voltage to be applied between the anode and the cathode to accelerate the thermoelectrons generated from the cathode of the X-ray tube, and an X-ray controller which controls X-ray irradiation conditions, such as the tube current of the high-voltage generation unit, the tube current thereof, the irradiation time, and the irradiation timing, in accordance with an instruction signal supplied from system control circuitry 16.

The image generation circuitry 6 includes projection data storage and image processing circuitry (neither is shown). The projection data storage sequentially stores time-series projection data supplied from the projection data generation circuitry 4 of the X-ray imaging unit 1 and generates two-dimensional projection data. On the other hand, the image processing circuitry generates image data by subjecting image processing, such as filtering processing, to the two-dimensional projection data generated by the projection data storage. In addition, the image processing circuitry performs synthesis processing, subtraction processing, etc. to a plurality of pieces of image data obtained. The image generation circuitry 6 described above can generate desired X-ray images, including two-dimensional X-ray fluoroscopic images, three-dimensional digital subtraction angiography (DSA) images, three-dimensional low contrast imaging (LCI) images and X-ray tomographic images.

The display 7 includes a main display device which displays medical images, etc., internal circuitry which supplies display signals to the main display device, and peripheral circuitry including connectors, cables, etc. to connect the main display device and the internal circuitry. The internal circuitry generates display data by superimposing supplemental information, such as information on the subject and projection data generation conditions, on image data supplied from the image operation circuitry of the image generation circuitry 6, performs digital-analog conversion and TV format conversion for the obtained display data, and displays the resultant image on the main display device.

The mechanism driving unit 10 comprises an imaging system moving mechanism driver 101 for supplying a driving signal to the movement mechanisms of the holding device 8 to move the imaging system in a desired direction, a couch top moving mechanism driver 102 for supplying a driving signal to the movement mechanism of the couch 9 to move the couch top in a desired direction, together with the subject 150 placed thereon, and a mechanism driving controller 103 for controlling the imaging system moving mechanism driver 101 and the couch top moving mechanism driver 102. The mechanism driving controller 103 has, for example, the function of controlling the imaging system moving mechanism driver 101, based on control information supplied from the system control circuitry 16, such that the movement or rotation of the imaging system provided for the holding unit is decelerated.

Next, a description will be given with reference to FIG. 2, as to how the holding device 8 and couch 9 are structured and how the units constituting them move or rotate. What are shown in FIG. 2 are: a holding device 8 whose holding unit 81 is a C arm to the ends of which the X-ray generator 2 and the X-ray detector 3 (imaging system) are attached; and a couch 9 having the couch top on which the subject 150 is placed. To facilitate the description given below, in FIG. 2, the body axis direction of the subject 150 (namely, the longitudinal direction of the couch top 91) is defined as a y axis, the direction of the central axis (the rotation axis) of a stand 83 holding the holding unit (C arm) 81 is defined as a z axis, and the direction perpendicular to both the y axis and the z axis is defined as an x axis.

The holding unit 81, to one end (lower end) of which the X-ray generator 2 is attached and to the other end (upper end) of which the X-ray detector 3 is attached in such a manner as to be opposed to the X-ray generator 2, is held by the stand 83 by means of a holding unit holder 82. The holding unit 81 is attached to the side face of the holding unit holder 82 such that the holding unit 81 is slidable in the direction of arrow a. The holding unit holder 82 is attached to the stand 83 such that the holding unit holder 82 is rotatable in the direction of arrow b, and the holding unit 81 is rotatable around the x axis in accordance with the rotation of the holding unit holder 82. The imaging system is attached to an end of the holding unit 81 such that the imaging system is slidable in the e direction. By utilization of the sliding movement of the holding unit 81 in the a direction, the rotation of the holding unit holder 82 in the b direction and the sliding movement of the imaging system in the e direction, the imaging system at the end of the holding unit 81 can be moved to any position or in any direction relative to the subject 150 placed on the couch top 91. The holding unit 81 and the holding unit holder 82 jointly constitute a holding device which holds the X-ray generator 2 and the X-ray detector 3 such that they are rotatable around the rotation axis x.

A floor swing arm 84 is installed on a floor surface 160. One end of the floor swing arm 84 is attached to the floor surface 160 such that the floor swing arm 84 is swingable around swing axis z1 (the first swing axis), and the stand 83 is attached to the other end of the floor swing arm 84 such that the stand 83 is swingable around swing axis z2 (the second swing axis). Both the swing axis z1 of the floor swing arm 84 and the swing axis z2 of the stand 83 extend in the z direction.

That is, the position information on the imaging system at the ends of the holding unit 81 is unambiguously determined by the sliding distance of the holding unit 81 relative to the holding unit holder 82, the rotating angle of the holding unit holder 82 in the b direction, the rotating angle of the floor swing arm 84 in the d direction, the rotating angle of the stand 83 in the c direction, and the sliding distance of the imaging system relative to the holding unit 81.

Therefore, the position information on the imaging system can be detected by detecting driving signals (for example, by counting the number of driving pulses) which are supplied from the imaging system moving mechanism driver 101 of the mechanism driving unit 10 to the movement mechanisms of the holding device 8 (namely, the holding unit sliding mechanism for sliding the holding unit 81, the holding unit holder rotation mechanism for rotating the holding unit holder 82 in the b direction, the stand rotation mechanism for rotating the stand 83 in the c direction, the floor swing arm rotation mechanism for rotating the floor swing arm 84 in the d direction, and the imaging system sliding mechanism for sliding the imaging system in the e direction) in order to move or rotate the holding unit 81, the holding unit holder 82, the stand 83 and the floor swing arm 84 in a predetermined direction. The couch body 92 of the couch 9 is provided with a horizontal movement mechanism for horizontally moving the couch top 91, on which the subject 150 is placed, in the body axis direction (the f direction), and a vertical movement mechanism for vertically moving the couch top 91 in the g direction.

In the present embodiment, the position information on the imaging system is detected by detecting an output of a first encoder (which detects the rotation of a driving motor driven by a driving signal) and an output of a second encoder (which detects the rotation of a load-side rotation axis), instead of detecting the driving signals themselves. To supplement the description, the rotation mechanism transmits the rotation of the driving motor mtr to the rotation axis e by means of a power transmission mechanism including a first belt vlt1, a worm reducer wrg, a first timing belt pulley tvp1, a second belt vlt2, a second timing belt pulley, etc., as in the example shown in FIG. 3. In the example shown in FIG. 3, the X-ray detector 3 (not shown) is rotated around the axis e of rotation in accordance with the rotation of the rotation axis e. The rotation mechanism includes the driving motor mtr and the power transmission mechanism.

In this type of rotation mechanism, the drive-side driving motor (servo motor) mtr incorporates the first encoder enc1. The second encoder (external encoder) enc2 is provided in the neighborhood of the load-side rotation axis. The structure in which the rotation or rotating movement is detected by the drive-side and load-side encoders enc1 and enc2 is employed for each of the rotation axes. For example, the holding unit holder rotation mechanism rotates the holding unit holder 82, which holds the holding unit 81, in the b direction by transmitting the rotation of the driving motor to the rotation axis by means of a power transmission mechanism including at least gears. A first encoder for detecting the rotation of the driving motor and a second encoder for detecting the rotation of the rotation axis are provided for the holding unit holder rotation mechanism mentioned above. The first encoder outputs a first pulse signal made up of a pulse train in accordance with the detection result of the rotation of the driving motor. The first pulse signal is supplied to the position information detector 11 through the imaging system moving mechanism driver 101. The second encoder outputs a second pulse signal made up of a pulse train in accordance with the detection result of the rotation of the rotation axis. The second pulse signal is supplied to the position information detector 11 through the imaging system moving mechanism driver 101. The "encoder" may be read as a "position detection sensor."

The position information detector 11 receives pulse signals from the movement mechanisms of the holding device 8 through the imaging system moving mechanism driver 101, and detects the position information on the holding unit 81 and the imaging system attached to the holding unit 81, based on the pulse signals.

The position information detector 11 includes first measurement circuitry 11a or second measurement circuitry 11b for measuring a backlash amount of the power transmission mechanism in parallel with the detection of the position information. The present embodiment will be described, referring to the case where the position information detector 11 includes the first measurement circuitry 11a.

Figure 4:
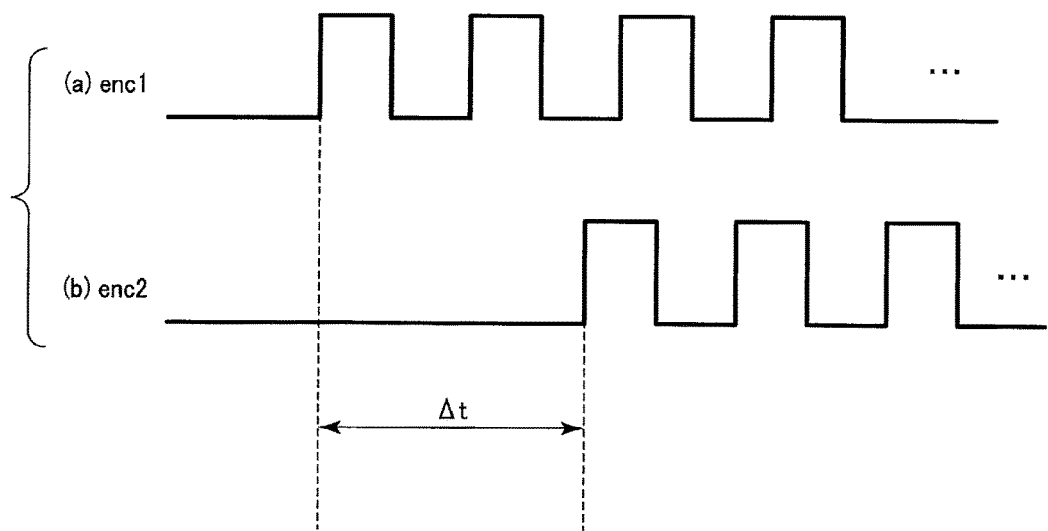
FIG. 4 is a waveform chart of a pulse signal of each encoder of the embodiment.

The first measurement circuitry 11a measures a difference value that indicates the time difference between a first pulse of the first pulse signal output from the first encoder enc1 and a corresponding second pulse of the second pulse signal output from the second encoder enc2, and regards the difference value as a value representing the looseness and backlash amount of the power transmission mechanism. To be more specific, the first pulse may be the leading pulse of the first pulse signal, and the second pulse may be the leading pulse of the second pulse signal. In this case, as shown in FIG. 4(a) and FIG. 4(b), the first measurement circuitry 11a measures a difference value that indicates time difference Δt between the leading pulse of the first pulse signal output from the first encoder enc1 and the leading pulse of the second pulse signal output from the second encoder enc2, and regards the difference value as a value representing the looseness and backlash amount of the power transmission mechanism. Time difference Δt may be the time interval between the rise times of the two leading pulses and may be measured by counting clock pulses (not shown) or by counting the pulses of the first pulse signal. Instead of using time difference Δt, for example, a count value of the clock pulses or a count value of the pulses of the first pulse signal may be used. In FIG. 4, time difference Δt between the rise times of the leading pulses included in the pulse trains of the pulse signals are shown schematically, and the pulse width and the pulse interval are not limited to those shown in FIG. 4. The first pulse and the second pulse are not limited to the leading pulses, and what is required is that they are pulses corresponding to each other.

The second measurement circuitry 11b is configured to measure a difference between pulse numbers, with the pulse number based on the gravitation direction being corrected. Specific details of this circuitry will be described later in connection with the second embodiment.

The first measurement circuitry 11a and the second measurement circuitry 11b may obtain a difference value, with the first pulse signal or the second pulse signal being inverted, or may obtain a difference value in association with a motor output current or torque. In such a case, the difference value can be controlled in accordance with an actual operation pattern or load.

The first measurement circuitry 11a and the second measurement circuitry 11b may supply a difference value or time difference obtained from the first pulse signal and the second pulse signal to the processing circuitry 13 such that the difference value or the time difference is associated with the accumulated total of the pulse values of each encoder and the operating speed. In this case, a history of the difference value associated with the accumulated total of pulse values and the operating speed is stored in the storage 12, so that abnormal states of the driving system can be detected, including looseness, a backlash and a movement in regions other than a gap.

The first measurement circuitry 11a and the second measurement circuitry 11b may be realized, for example, by a ROM (not shown) storing programs and a processor (not shown) executing the programs in the ROM. For example, the first measurement circuitry 11a and the second measurement circuitry 11b may be realized as a function of the processing circuitry 13.

The position information detector 11 detects position information on the couch top 91 of the couch 9, based on driving signals supplied from the couch top moving mechanism driver 102 to the movement mechanisms of the couch 9.

The storage 12 includes a memory (e.g., a hard disk drive (HDD)) for storing electric information, and peripheral circuitry related to the memory, such as a memory controller and a memory interface. The storage 12 stores programs that are executed by the system control circuitry 16 and the processing circuitry 13, and also stores a history of difference values written by the processing circuitry 13. The history of difference values includes difference values which are associated with dates and times for each rotation axis (or holding unit). Where a value corresponding to a difference value represents a gear backlash amount, the history of difference values can be plotted, as in the graph shown in FIG. 5. On the ordinate axis of the graph, the gear backlash amount is expressed as a length into which the pulse number corresponding to the difference value obtained by the first measurement circuitry 11a or the second measurement circuitry 11b is translated. On the abscissa axis of the graph, a history of the date and time is expressed as the year and month. Sample A and sample B in the graph correspond to rotation axes (or rotation mechanisms). The reference value of the maintenance requirement determination shown in the graph is an example of a value that triggers determination of either a secular change or a sudden event, and is stored in the storage 12. The "secular change" is an example of a "temporal change."

The processing circuitry 13 is a processor which reads and executes processing programs in the storage 12 and which realizes the log function 13a, determination function 13b and output function 13c corresponding to the programs. The processing circuitry 13 may be a processor for realizing the functions of the first measurement circuitry 11a and the second measurement circuitry 11b, in addition to the log function 13a, determination function 13b and output function 13c mentioned above. In this case, the processing circuitry 13 detects an abnormal state of the power transmission mechanism, for example, based on the time difference between a first pulse of the first pulse signal output from the first encoder and a corresponding second pulse of the second pulse signal output from the second encoder. In FIG. 1, the single processing circuitry 13 is shown as realizing the log function 13a, the determination function 13b and the output function 13c. In place of this, the processing circuitry 13 may be a combination of independent processors, and these processors may execute the programs to realize the respective functions. The functions mentioned here may include the functions of the first measurement circuitry 11a and the second measurement circuitry 11b.

The log function 13a is the function of storing operation records of the medical image diagnostic apparatus 100 in the storage 12. The operation records are provided, for example, by the position information detector 11, the system control circuitry 16 and the processing circuitry 13. For example, upon reception of a difference value received from the first measurement circuitry 11a (or second measurement circuitry 11b), the log function 13a associates a date and time with the difference value and stores a history of the difference value in the storage 12.

If the difference value exceeds the reference value, the determination function 13b determines whether the cause of the exceedance of the reference value is a temporal change or a sudden event, based on how the time difference is before the reference value stored in the storage 12 is exceeded and how the difference value changes after the reference value is exceeded.

If the difference value exceeds the reference value, the determination function 13b may determine whether the cause of the exceedance of the reference value is a secular change or a sudden event, based on the difference value taken immediately before the reference value is exceeded and the rate of change at which the difference value changes when the reference value is exceeded. The determination function 13b may provide the result of determination to the log function 13a as log information such that log information including the date and time and the result of determination is stored in the storage 12.

The output function 13c is the function of outputting processing results from the processing circuitry 13. For example, the output function 13c outputs determination results obtained by the determination function 13b. The processing results and the determination results are supplied, for example, to the display 7, the alarm generator 14 and the system control circuitry 16. In response to access made from the input interface 15, the output function 13c can output the log information stored in the storage 12.

The output function 13c may supply a determination result to the call center of an apparatus manufacturer or the like through the Internet or the like, by using a remote maintenance system such as InnerVision™. In this case, the technical person who receives contact from the call center or the like can start a maintenance operation in accordance with the determination result, so that maintenance can be performed efficiently.

The alarm generator 14 is provided, for example, with a buzzer or a speaker (neither is shown in the drawings), and generates an alarm based on an error output supplied from the processing circuitry 13 or the system control circuitry 16.

The input interface 15 is realized by a trackball, a switch button, a mouse, a keyboard, which are used for setting a region of interest (ROI), a touch pad which performs an input operation when the operation surface thereof is touched, a touch panel display in which an integrated display screen and a touch pad are integrated, etc. The input interface 15 is connected to the system control circuitry 16, converts an input operation received from the operator into an electric signal, and supplies the electric signal to the system control circuitry 16. In the present specification, the input interface 15 is not limited to physical operation members such as a mouse and a keyboard. For example, the input interface 15 can include electric signal processing circuitry which receives an electric signal corresponding to an input operation from an external input device separate from the apparatus and which supplies the electric signal to the system control circuitry 16.

The system control circuitry 16 includes a processor and a memory (neither is shown), and various information entered or set by the input interface 15 is stored in the memory. Based on the input information and setting information, the processor integratedly controls the units of the medical image diagnostic apparatus 100 such that safe and efficient X-ray imaging can be performed for the subject 150.

In addition, the system control circuitry 16 has the function of allowing, stopping or restricting X-ray imaging at the time of error occurrence, based on whether the determination result by the processing circuitry 13 indicates a temporal change or a sudden event. For example, where the determination result indicates a temporal change, the rotation mechanism of the holding device 8 includes worn portions and has an increased backlash amount. Although the rotation mechanism has no problems in terms of the safety, it deteriorates in performance. For example, where the determination result indicates a sudden event, it is likely that the rotation mechanism of the holding device 8 is damaged. In this case, parts may be broken and fall. Therefore, where the determination result indicates a temporal change, the system control circuitry 16 determines that there is no problem in terms of the safety and that X-ray imaging can be performed. That is, the system control circuitry 16 allows X-ray imaging in a restricted manner or prevents it in consideration of the deterioration in performance. Where the determination result indicates a sudden event, the system control circuitry 16 determines that there may be a damaged portion and prevents or restricts the X-ray imaging.

Next, an operation of the medical image diagnostic apparatus having the above configurations will be described.

Prior to the X-ray imaging of the subject 150, the operator of the medical image diagnostic apparatus 100 operates the input interface 15 to enter subject information and X-ray irradiation conditions. In addition, the operator moves or rotates the imaging system attached to the holding unit (C arm) 81 of the holding device 8 and the couch top 91 of the couch 9 (on which the subject 150 is placed) to predetermined positions (initial positions).

When the couch top 91 and the imaging system are moved or rotated, the position information detector 11 detects initial position information on the couch top 91, based on driving signals which are supplied from the couch top moving mechanism driver 102 of the mechanism driving unit 10 to the horizontal movement mechanism and vertical movement mechanism of the couch 9.

In the meantime, the holding unit 81 and the driving motor of the imaging system attached to the holding unit 81 are rotated, based on driving signals which are supplied from the imaging system moving mechanism driver 101 to the holding unit sliding mechanism, holding unit holder rotation mechanism, stand rotation mechanism, floor swing arm rotation mechanism and imaging system sliding mechanism of the holding device 8. Each rotation mechanism rotates the holding device 8 by transmitting the rotation of the driving motor to the rotation axis by means of a power transmission mechanism including at least gears. Likewise, each sliding mechanism slides the holding unit 81 or the imaging system by transmitting the rotation of the driving motor by means of a power transmission mechanism including at least gears.

Each of the rotation mechanisms of the holding device 8 receives a first pulse signal output from the first encoder (which is for detecting the rotation of the driving motor driven with a driving signal) and a second pulse signal output from the second encoder (which is for detecting the rotation of the load-side rotation axis) and supplies these pulse signals to the position information detector 11 by way of the imaging system moving mechanism driver 101.

The position information detector 11 detects initial position information, based on the first and second pulse signals supplied thereto. Likewise, the position information detector 11 detects position information on the holding unit 81 and imaging system that are moving, based on the first and second pulse signals which are supplied from the imaging system moving mechanism driver 101 in accordance with the movement of the imaging system and the initial position information on the holding unit 81 and the imaging system.

In parallel with the detection of the initial position information and the position information, the first measurement circuitry 11a of the position information detector 11 measures a backlash amount of the power transmission mechanism.

To be more specific, the first measurement circuitry 11a measures time difference Δt between the leading pulse of the first pulse signal and the leading pulse of the second pulse signal as a value corresponding to the looseness and backlash amount of the power transmission mechanism. The measured difference value is supplied to the processing circuitry 13.

Upon reception of a difference value received from the first measurement circuitry 11a, the log function 13a of the processing circuitry 13 associates the difference value with a date and time and stores a history of the difference value in the storage 12.

In this manner, the history of the difference value is stored in the storage 12 in parallel with the operation of detecting position information in accordance with the movement or rotation of the holding device 8.

Next, the operator starts X-ray fluoroscopy of the subject 150 by entering an X-ray fluoroscopy start command from the input interface 15, and moves the imaging system to a desired position while observing the fluoroscopic image data generated by the X-ray imaging unit 1 and image generation circuitry 6.

Next, the operator moves or rotates the imaging system at low speed while observing the fluoroscopic image data, and when the imaging system is moved and set at the desired position on the subject 150, the operator operates the input interface 15 to enter a command signal for stopping the movement or rotation of the imaging system and a command signal for starting X-ray imaging.

Upon reception of these command signals, the system control circuitry 16 executes X-ray imaging for the subject 150 under the preset X-ray imaging conditions.

During the X-ray fluoroscopy and X-ray imaging, a history of the difference value is stored in the storage 12 in parallel with the operation of detecting position information in accordance with the movement or rotation of the holding device 8.

In addition, the determination function 13b of the processing circuitry 13 compares the difference value with the reference value. When the difference value exceeds the reference value, the determination function 13b calculates a rate of change based on the difference value measured immediately before the reference value in the storage 12 is exceeded and the difference value measured when the reference value is exceeded. Further, the determination function 13b of the processing circuitry 13 determines whether the cause of the exceedance of the reference value is a secular change or a sudden event, based on the calculated rate of change. To be specific, where the rate of change is not more than a threshold value, the cause of the exceedance of the reference value is regarded as a secular change. Where the rate of change is more than the threshold value, the cause of the exceedance is regarded as a sudden event. The technical person determines what should be maintained in accordance with the cause.

For example, in the example illustrated in FIG. 5, the gear backlash amount of sample A exceeds the reference value in November of 2015, and it is determined that the cause of the exceedance is a secular change. In this case, maintenance is required.

The gear backlash amount of sample B exceeds the reference value in June of 2015, and it is determined that the cause of the cause of the exceedance is a sudden event. In this case, maintenance is required.

In the case of sample A, the exceedance is attributed to the secular change occurred in the normal use state, and it is determined that the backlash can be dealt with by making ordinary adjustment.

In the case of sample B, the reference value is exceeded in an overload condition such as the condition where a shock load is applied, and it is determined that the backlash cannot be dealt with by making ordinary adjustment and that all parts that are related to the strength of the mechanism have to be checked. FIG. 5 shows the case where the backlash amount continues to increase even after July of 2015. In actuality, however, all parts are checked within several hours of the occurrence of the sudden event, and adjustment is made to reduce the backlash amount.

After this, the output function 13c of the processing circuitry 13 supplies a determination result to the display 7, alarm generator 14 and system control circuitry 16.

The display 7 displays the determination result. The alarm generator 14 outputs an alarm sound in accordance with the determination result. The system control circuitry 16 restricts the X-ray imaging and the movement or rotation of the holding device 8 in accordance with the determination result.

As described above, according to the present embodiment, the holding device 8 is rotated by transmitting the rotation of the driving motor to the rotation axes by means of a power transmission mechanism including at least gears. The first encoder detects the rotation of the driving motor. The second encoder detects the rotation of the rotation axis. An abnormal state of the power transmission mechanism is detected based on the time difference between a first pulse of the first pulse signal output from the first encoder and a corresponding second pulse of the second pulse signal output from the second encoder.

Accordingly, the present embodiment eliminates the need for a visual check, which was performed regularly in the past, and the low operation rate caused by the regular check can be prevented. To be more specific, a difference value representing the time difference between the leading pulse of the first pulse signal output from the first encoder and the leading pulse of the second pulse signal output from the second encoder is measured as a value corresponding to the looseness and backlash amount of the power transmission mechanism.

In the above description, reference was made to the case where the looseness and backlash amount were evaluated based on the time difference between the leading pulse of the first pulse signal and the leading pulse of the second pulse signal. Needless to say, the time difference does not have to be that between leading pulses. For example, the looseness and the backlash amount may be evaluated based on the leading pulse of the first pulse signal and the second pulse signal. That is, any pulse of the first pulse signal and the corresponding pulse of the second pulse signal may be used.

In addition to the above, according to the present embodiment, a history of difference values is stored. If a difference value exceeds the reference value, determination is made as to whether the cause of the exceedance of the reference value is a temporal change or a sudden event, based on how the time difference is before the reference value is exceeded and how the difference value changes after the reference value is exceeded. To be specific, whether the cause of the exceedance of the reference value is a temporal change or a sudden event is determined, based on the difference value taken immediately before the reference value is exceeded and the rate of change at which the difference value changes when the reference value is exceeded.

As described above, the history of difference values are managed, and how the time difference or the rate of change of the difference value changes before and after the exceedance of the reference value is examined. By so doing, it can be determined whether the cause of the exceedance of the reference value is attributable to a secular change or a sudden event such as collision. Accordingly, proper maintenance and operational management of service can be performed in accordance with the cause. As a result, the imaging and the treatment under fluorescence can be continued without unnecessarily stopping the use of the medical image diagnostic apparatus 100. In addition, since a proper check operation can be performed in accordance with the condition of the apparatus, the maintenance operation can be performed efficiently.

In the first embodiment, the brakes may be checked in addition to the looseness and backlash amount of the power transmission mechanism. To be specific, a driving signal is supplied to the driving motor, with a load-side rotation axis braked, and the rotation of the load-side rotation axis is detected by the second encoder.

In more detail, the driving signal is supplied to the driving motor in the braked state, and whether or not a second pulse signal is output from the second encoder is checked. If the second pulse signal is output, it follows that the load-side rotation axis is rotated.

If the load-side rotation axis is rotated, it is determined that the brake does not work, and the necessity of a check is indicated on the display 7. If the load-side rotation axis is not moved, the current value of the driving motor is gradually increased, and the condition of the load-side rotation axis is checked. If the load-side axis is moved when the current value is not more than a threshold value, then it is determined that the braking force is insufficient, and the necessity of a check is indicated on the display 7.

This brake check is also applicable to the embodiments set forth below.

Second Embodiment

A medical image diagnostic apparatus according to the second embodiment will be described with reference to FIG. 1.

The second embodiment is a modification of the first embodiment. In place of the first measurement circuitry 11a that measures a time difference between pulse signals, the second measurement circuitry 1ib corrects a pulse number based on the gravitation direction and measures a difference in pulse number. The pulse number is the number of pulses. The other configurations are similar to those of the first embodiment.

The second measurement circuitry 11b includes a translation unit, a correction unit and a difference value measurement unit. The translation unit translates the pulse number of the first pulse signal into a pulse number of the second pulse signal, thereby obtaining a translation pulse number. The correction unit corrects the translation pulse number in accordance with a rotation start angle and a rotation end angle such that the corrected pulse number does not include a pulse number corresponding to a slight rotation which the holding unit 81 and the holding unit holder 82 make due to the gravitation direction. The difference value measurement unit measures a difference value between the corrected translation pulse number and the pulse number of the second pulse signal as a value corresponding to the backlash amount of the power transmission mechanism.

Figure 6:
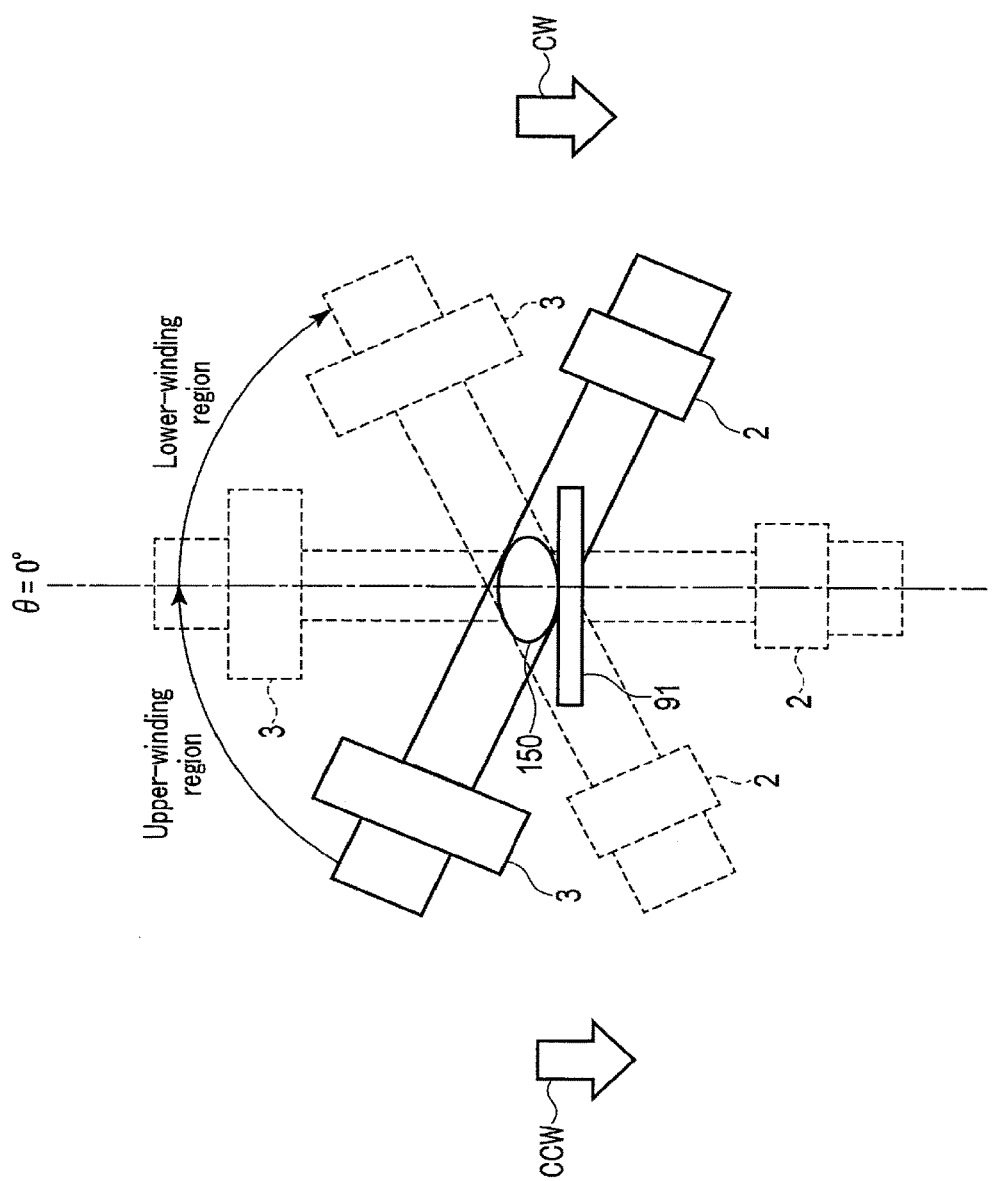
FIG. 6 is a schematic diagram illustrating how a backlash amount is corrected in a medical image diagnostic apparatus according to a second embodiment.

To supplement the description, the multi-axis rotation type holding device 8 including a C arm or the like undergoes reversal of gravitation direction CCW, CW between the upper-winding region of the arm and the lower-winding region of the arm, as shown in FIG. 6. As a result, the direction of the slight backlash amount applied to the rotation axis of the arm reverses. For this reason, the backlash amount of the rotation axis cannot be accurately measured by merely detecting the difference between the pulse number of the first pulse signal of the driving motor and the pulse number of the second pulse signal of the load-side rotation axis.

The second measurement circuitry 11b calculates a difference value relating to the axis in accordance with the position information on the rotation axis which undergoes a change in the gravitation direction. For example, in the case of a rotation axis whose gravitation direction reverses vertically, the measurement value of the backlash amount of the rotation axis is corrected in accordance with the gravitation direction (a slight backlash amount is added or subtracted), based on the position information on the rotation axis in the gravitation direction. By this correction, the effect of the change of position is eliminated and accurate control is thus enabled.

Figure 7:
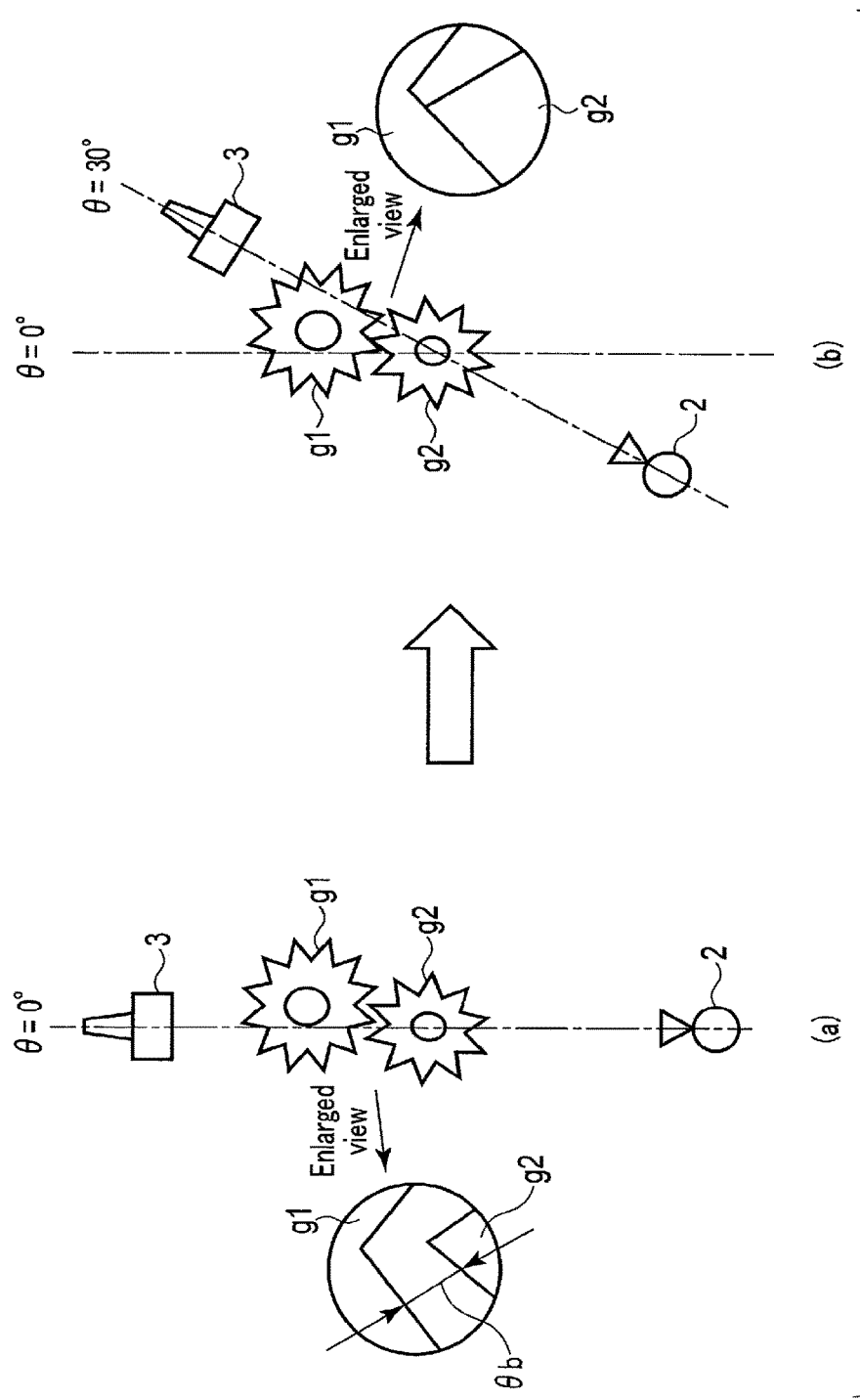
FIG. 7 is a schematic diagram illustrating how a backlash amount is corrected in the embodiment.
Figure 8:
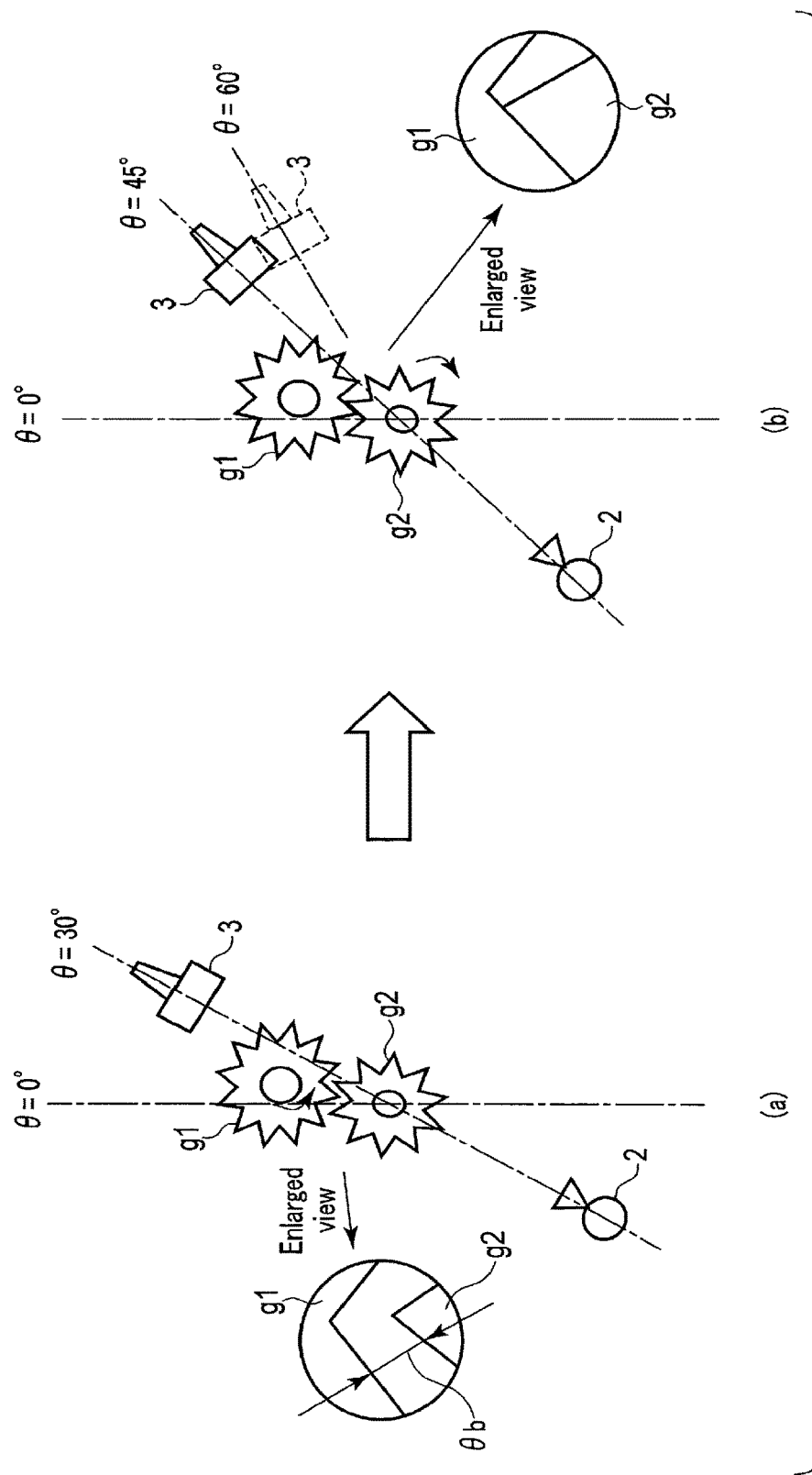
FIG. 8 is a schematic diagram illustrating how a backlash amount is corrected in the embodiment.

How the medical image diagnostic apparatus of the above configuration measures a backlash amount will be described with reference to the schematic diagrams in FIGS. 7 and 8. In the description below, reference will be made to (1) an example in which the holding unit is inclined from the upright state, (2) an example of a lower-winding operation and (3) an example of an upper-winding operation. In FIG. 7 and FIG. 8, the holding unit 81 corresponds to the central axes (long dashed short dashed lines) of the X-ray generator 2 and the X-ray detector 3 which are opposed to each other.
(1) Example of How Holding Unit Is Inclined from Upright State: Measurement Example in 0° to 30° Interval Let us assume that the holding unit 81 is in the state in which the linear line connecting between the X-ray generator 2 and the X-ray detector 3 and the vertical line form an angle θ of 0°, as shown in FIG. 7(a) (θ=0: Upright State). At this time, backlash θb corresponding to, for example, two pulses is present between the drive-side first gear g1 and the load-side second gear g2 driven by the first gear g1. In other words, a gap (θb) is present between the first gear g1 and the second gear g2 when the holding unit 81 in the upright state begins to move.

Let us assume that the holding unit 81 is inclined clockwise by 30° from the upright state, as shown in FIG. 7(b). After the holding unit 81 is inclined, the gap (θb) is not present between the first gear g1 and the second gear g2.

Therefore, the second encoder outputs a second pulse having the following pulse number when the holding unit 81 is inclined from 0° to 30°.

> Pulse Number of Second Pulse Signal=(Initial Pulse Number)+(Pulse Number Corresponding to Rotation Angle)=2 Pulses+Pulse Number Corresponding to 30°

That is, the pulse number of the second pulse signal includes 2 pulses corresponding to the backlash (play, slipping) at the start of movement, in addition to the number of pulses corresponding to the rotation angle (30°).

On the other hand, the first encoder outputs a first pulse signal having the pulse number corresponding to 30°, in accordance with the rotation of the drive-side first gear g1.

Therefore, the second measurement circuitry 11b obtains a translation pulse number by translating the pulse number (i.e., the pulse number corresponding to 30°) of the first pulse signal into a pulse number of the second pulse signal.

The second measurement circuitry 11b corrects the translation pulse number in accordance with a rotation start angle (0°) and a rotation end angle (30°), such that the corrected pulse number does not include a pulse member resulting from a slight rotation which the holding unit 81 and the holding unit holder 82 make due to the gravitation direction. In the 0° to 30° interval, the correction is not performed because there is no pulse number which is due to the gravitation direction.

The second measurement circuitry 11b measures a difference value (two pulses) between the corrected translation pulse number (pulse number corresponding to 30° and the pulse number of the second pulse signal (two pulses+pulse number corresponding to (30°) as a value corresponding to the backlash amount of the power transmission mechanism. The second measurement circuitry 11b may translate the difference value of "two pulses" into a backlash amount and regard this backlash amount as a difference value. In either case, the measured difference value is supplied to the processing circuitry 13.

Thereafter, the processing circuitry 13 stores a history of the difference value in the storage 12 and performs processing corresponding to the determination function 13b and output function 13c in the manner described above.

(2) Example of Lower-Winding Operation: Measurement Example in 30° to 60° Interval Let us assume that the holding unit 81 is in the state in which the linear line connecting between the X-ray generator 2 and the X-ray detector 3 and the vertical line form an angle θ of 30°, as shown in FIG. 8(*a*) (θ=30: Inclined State). At this time, backlash θb corresponding to, for example, two pulses is present between the drive-side first gear g1 and the load-side second gear g2. In other words, a gap (θb) is present between the first gear g1 and the second gear g2 when the holding unit 81 in the inclined state begins to move.

Let us assume that the holding unit 81 is inclined clockwise by an angle in the range of 15° to 30° from the inclined state, as shown in FIG. 8(*b*))(45°<θ≤60°). After the holding unit 81 is inclined, the load-side second gear g2 makes a slight rotation, due to the weight of the holding unit 81, and the holding unit 81 is further inclined by an angle corresponding to two pulses. The gap (θb) is not present between the first gear g1 and the second gear g2.

Therefore, the second encoder outputs a second pulse having the following pulse number when the 30°-inclined holding unit 81 is further inclined by an angle in the range of 15° to 30° (45°<θ≤60°).

> Pulse Number of Second Pulse Signal=(Initial Pulse Number)+(Pulse Number Corresponding to Rotation Angle)−(Pulse Number Corresponding to Slight Rotation Caused by Gravity)=2 Pulses+Pulse Number Corresponding to 30°−2 Pulses As can be seen from this, the two pulses included in the second pulse signal and corresponding to the backlash (play, slipping) at the start of movement are canceled by the two pulses corresponding to the slight rotation caused by the gravity. Therefore, correction must be performed such that the two pulses corresponding to the slight rotation caused by the gravity are not included.

On the other hand, the first encoder outputs a first pulse signal having the pulse number corresponding to 30° in accordance with the rotation of the drive-side first gear g1.

Therefore, the second measurement circuitry 11b obtains a translation pulse number by translating the pulse number (pulse number corresponding to 30°) of the first pulse signal into a pulse number of the second pulse signal.

The second measurement circuitry 11b corrects the translation pulse number (subtracts two pulses) in accordance with the rotation start angle (30°) and the rotation end angle (60°), such that the corrected pulse number does not include a pulse member (two pulses are subtracted) resulting from a slight rotation which the holding unit 81 and the holding unit holder 82 make in the gravitation direction (CW).

The second measurement circuitry 11b measures a difference value (two pulses) between the corrected translation pulse number (the pulse number corresponding to 30°−two pulses) and the pulse number of the second pulse signal (two pulses+the pulse number corresponding to 30°−two pulses) as a value corresponding to the backlash amount of the power transmission mechanism. The second measurement circuitry lib may translate the difference value of two pulses into a backlash amount and regard this backlash amount as a difference value. In either case, the measured difference value is supplied to the processing circuitry 13.

Thereafter, the processing circuitry 13 stores a history of the difference value in the storage 12 and performs processing corresponding to the determination function 13b and output function 13c in the manner described above.

As described above, according to the present embodiment, the pulse number of the first pulse signal is translated into a pulse number of the second pulse signal, thereby obtaining a translation pulse number. In addition, the translation pulse number is corrected in accordance with a rotation start angle and a rotation end angle, such that the corrected pulse number does not include a pulse member resulting from a slight rotation which the holding device (the holding unit 81 and the holding unit holder 82) makes due to the gravitation direction. A difference value between the corrected translation pulse number and the pulse number of the second pulse signal is measured as a value corresponding to the backlash amount of the power transmission mechanism.

Therefore, since the correction is performed in such a manner as not to include the slight rotation which is due to the gravitation direction, the present embodiment has not only the advantages of the first embodiment but also the advantage that the backlash amount can be measured with high accuracy in consideration of the position at the time of measurement.

According to the present embodiment, the correction can be performed not only based on the difference value between the motor encoder and the rotation axis (load-side) encoder but also in combination with other control parameters such as the position at the time of measurement (relative to the gravitation direction). Therefore, the backlash amount of mechanisms can be measured in consideration of an actual motion load. Accordingly, highly accurate and precise maintenance is enabled. The output torque and current value of the driving motor may be combined as other control parameters.

The present embodiment can be modified as follows: If the difference value corresponding to the backlash amount includes an error of a slight rotation which is due to the gravitation direction, the correction mentioned above does not have to be performed and a history of the difference value does not have to be stored. For example, if a rotation starts in the state where the angle between the linear line connecting the X-ray generator 2 and the X-ray detector 3 and the vertical line (i.e., the gravitation direction) is not more than 30° and the rotation ends in the state where the above angle is within the range of 45° to 60°, the processing circuitry 13 may omit storing the difference value in the storage 12. Even in this modification, the influence of the slight rotation which is due to the gravitation direction can be eliminated from the difference value whose history is stored. Accordingly, highly accurate and precise maintenance is enabled.

Third Embodiment

A medical image diagnostic apparatus according to the third embodiment will be described.

The third embodiment is a specific example of the first or second embodiment, and the entire control flow, a position information reading flow and a log output flow will be described in connection with the third embodiment.

When executing the entire control flow, the position information reading flow and the log output flow, the medical image diagnostic apparatus 100 is configured to perform operations similar to those described in connection with the first and second embodiments.

Each of the flows performed by the medical image diagnostic apparatus of the above configuration will be described with reference to FIGS. 9 through 11.

Figure 9:
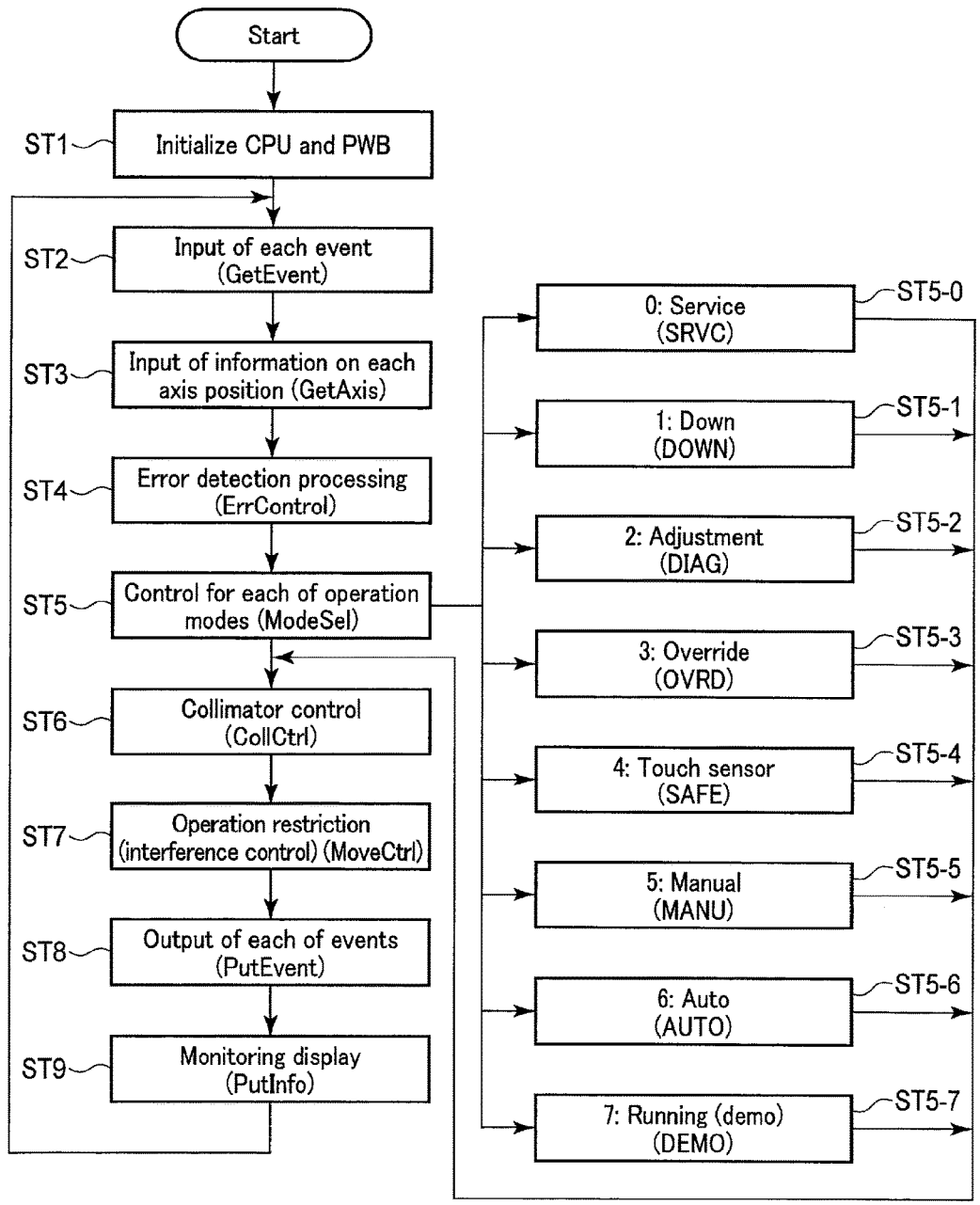
FIG. 9 is a flowchart illustrating the overall operation of a medical image diagnostic apparatus according to a third embodiment.

As shown in FIG. 9, the medical image diagnostic apparatus 100 first initializes the CPU and PWB (step ST1) in response to an operator's operation, and then repeatedly performs steps ST2 to ST9.

After step ST1, processes including input of each event (GetEvent) (step ST2), input of information on each axis position (GetAxis) (step ST3), error detection processing (ErrControl) (step ST4), control for each of operation modes (ModeSel) (step ST5), collimator control (CollCtrl) (step ST6), operation restriction (interference control) (MoveCtrl) (step ST7), output of each of events (PutEvent) (Step ST8) and monitoring display (PutInfo) (step ST9), are repeatedly executed.

The operation modes in step ST5 are service (SRVC) (step ST5-0), down (DOWN) (step ST5-1), adjustment (DIAG) (step ST5-2), override (OVRD) (step ST5-3), touch sensor (SAFE) (step ST5-4), manual (MANU) (step ST5-5), auto (AUTO) (step ST5-6), and running (demo) (DEMO) (step ST5-7).

The service mode in step ST5-0 is a mode used by a serviceperson.

The down mode in step ST5-1 is a mode in which a fallback operation is executed. In the down mode, if an error occurs, the axis related to the error is stopped, and another axis is operated. If all axes are stopped, a catheter placed into a subject has to be pulled out in a blind way, and it is therefore desired that the ongoing inspection be continued in a limited or restricted manner.

For example, if an error occurs in the auto mode or manual mode, the down mode is selected and executed in place of such a mode. Also, the down mode is a mode in which the operation of the rotation axis whose difference value exceeds the reference value is stopped, and the operation of another rotation axis is enabled.

The adjustment mode in step ST5-2 is a mode selected when an inspection or adjustment is performed. For example, the adjustment mode is a mode in which a backlash is adjusted.

The override mode in step ST5-3 is a mode in which the holding unit 81 entering an interference region and stopping there is slowly moved with an alarm sound generated, in response to an operation of the override switch of the console.

The touch sensor mode in step ST5-4 is a special mode used when a contact safety switch attached to the X-ray generator 2, X-ray detector 3 and holding unit 81 touches something and outputs a detection signal. In the touch sensor mode, the related rotation axis is stopped and a movement away from the rotation axis is automatically performed.

The manual mode in step ST5-5 is a mode in which the holding unit 81 or the like is operated like a radio-controlled unit in response to an operation of the operation lever by the operator.

The auto mode in step ST5-6 is a mode in which a number is selected and an operation is performed in accordance with a program stored in a memory. In the auto mode, X-ray imaging is executed, for example, in accordance with a selected image-capturing sequence.

The running (demo) mode in step ST5-7 is a mode in which a predetermined operation is executed for a demonstration purpose.

The processing circuitry 13 makes a determination in the modes mentioned above, for example, in the auto mode in which X-ray imaging is executed in accordance with a predetermined image-capturing sequence or in the manual mode in which processing is performed in response to an operation by the operator. When the result of determination indicates a sudden event, the system control circuitry 16 switches the auto mode or manual mode to the down mode and restricts the X-ray imaging or the rotation of the rotation axis. At this time, in the down mode, the operation of the rotation axis whose difference value exceeds the reference value is stopped, and the operation of another rotation axis is enabled.

Next, a description will be given of how the information on each axis position is input in step ST3.

Figure 10:
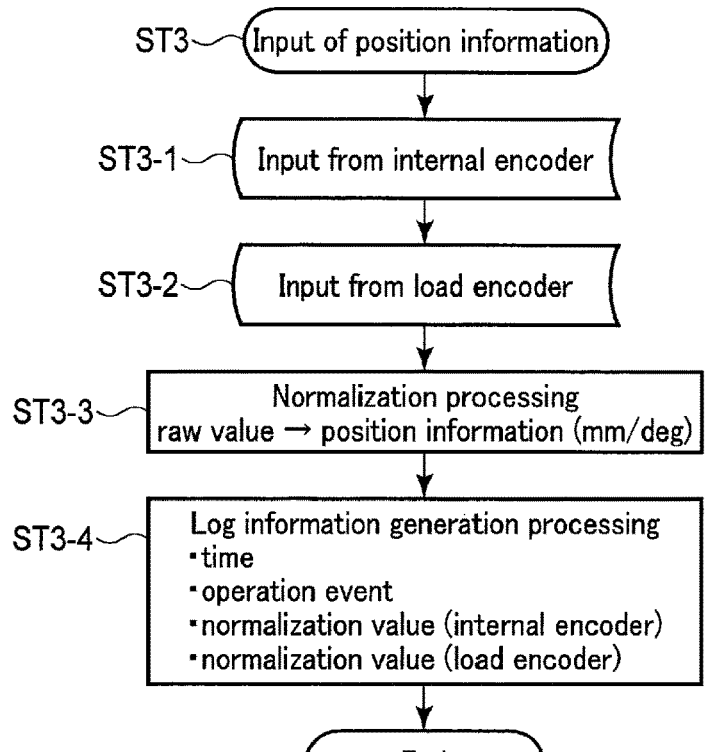
FIG. 10 is a flowchart illustrating how position information is read in the embodiment.

The medical image diagnostic apparatus 100 executes the position information reading processing of step ST3 (steps ST3-1 to ST3-4), as shown in FIG. 10.

The first encoder, also referred to as an internal encoder, detects the rotation of the driving motor driven by a driving signal and supplies a first pulse signal having a pulse train corresponding to the detection result to the position information detector 11 through the imaging system moving mechanism driver 101 (step ST3-1).

The second encoder, also referred to as a load encoder, detects the rotation of the load-side rotation axis and supplies a second pulse signal having a pulse train corresponding to the detection result to the position information detector 11 through the imaging system moving mechanism driver 101 (step ST3-2).

The position information detector 11 performs normalization processing in which the pulse number (raw value) of the first pulse signal is translated into position information and the pulse number (raw value) of the second pulse signal is translated into position information (step ST3-3). The two normalization values of the position information are supplied to the processing circuitry 13.

The processing circuitry 13 generates log information by adding a time and an operation event to the received normalization values (step ST3-4).

Step ST3 is completed when the processing in steps ST3-1 to ST3-4 is executed for each of the axes.

Next, a description will be given of how log output, an example of output of events in Step ST8, is performed.

Figure 11:
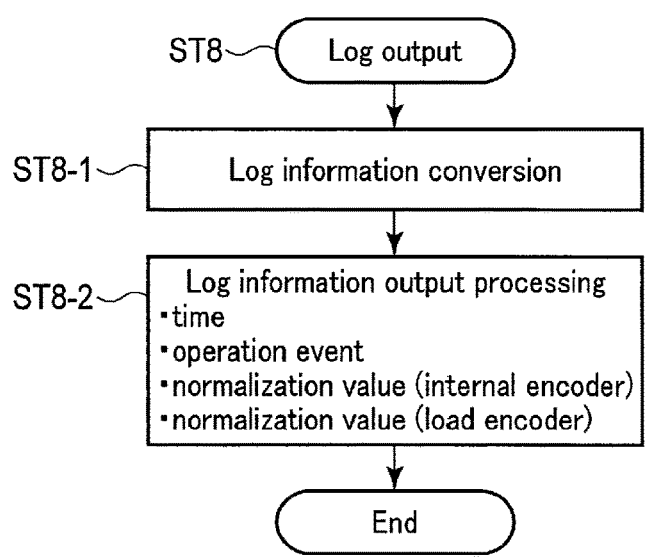
FIG. 11 is a flowchart illustrating how log output processing is performed in the embodiment.

The medical image diagnostic apparatus 100 executes log output processing (steps ST8-1 and ST8-2) as part of step ST8, as shown in FIG. 11.

The processing circuitry 13 converts the log information on each axis obtained in step ST3-4 into information of predetermined format (step ST8-1). In addition, the processing circuitry 13 outputs the converted log information to the storage 12 (step ST8-2).

As described above, according to the present embodiment, a determination is made either in the auto mode in which X-ray imaging is executed in accordance with a predetermined image-capturing sequence or in the manual mode in which processing is performed in response to an operation by the operator. Further, the auto mode or manual mode is switched into the down mode, in which the operations are restricted. The down mode is a mode in which the operation of the rotation axis whose difference value exceeds the reference value is stopped and the operation of another rotation axis is enabled.

According to the present embodiment, therefore, the advantages of the first or second embodiment are obtained, and the auto mode or manual mode can be smoothly switched to the down mode at the time of error occurrence. As a result, the imaging and the treatment under fluorescence can be continued without unnecessarily stopping the use of the medical image diagnostic apparatus 100.

Fourth Embodiment

A medical image diagnostic apparatus according to the fourth embodiment will be described with reference to FIG. 12 and FIG. 13.

The fourth embodiment is a specific example of each of the first to third embodiments, and a detailed description will be given as to how the system control circuitry 16 allows, prevents or restricts X-ray imaging, based on whether the determination result obtained by the processing circuitry 13 indicates a temporal change or a sudden event.

The system control circuitry 16 has a first prevention function, an allowance function, a second prevention function and a restriction function. Where the determination result indicates a temporal change, the rotation mechanism of the holding device 8 includes worn portions and has an increased backlash amount. Although the rotation mechanism has no problems in terms of the safety, it deteriorates in performance. Where the determination result indicates a sudden event, it is likely that the rotation mechanism of the holding device 8 is damaged. In this case, parts may be broken and fall.

The first prevention function is a function of preventing execution of X-ray imaging if the determination result indicates a temporal change and an X-ray image to be produced by the X-ray imaging performed during rotation of the holding unit 81 is low in image quality, In the column of "Secular change (sample A)" shown in FIG. 12, the execution of 3D-LCI imaging is prevented.

The allowance function is a function of allowing the execution of the X-ray imaging if the X-ray image is high in image quality. In the column of "Secular change (sample A)" shown in FIG. 12, the execution of rotation DSA imaging and 3D-DSA imaging is allowed. In the column of "secular change (sample A)" shown in FIG. 13, the execution of all operations is allowed.

The second prevention function is a function of preventing the execution of X-ray imaging if the determination result indicates a sudden event. In the column of "Sudden event (sample B)" shown in FIG. 12, the execution of rotation DSA imaging, 3D-DSA imaging and 3D-LCI imaging is prevented.

If the determination result indicates a sudden event and if an X-ray image is to be produced by the X-ray imaging after the holding unit 81 is rotated, the restriction function restricts the operation of each of the rotation mechanisms of the holding device 8. In this case, the restriction function restricts the operation of each rotation mechanism, for example, such that a fallback operation is performed at low speed. In the column of "Sudden event (sample B)" shown in FIG. 12, the operating speed, the operating range and the acceleration/deceleration control parameter are restricted. In this case, the operating speed is decreased. The operating range is controlled such that an operation is enabled only within the range determined in the gravitation direction at the time of error occurrence. The acceleration/deceleration control parameters are controlled such that an acceleration/deceleration time lengthens. In the column of "Sudden event (sample B)" shown in FIG. 13, the execution of all operations is restricted.

The other configurations are similar to those of the first to third embodiments.

Figure 14:
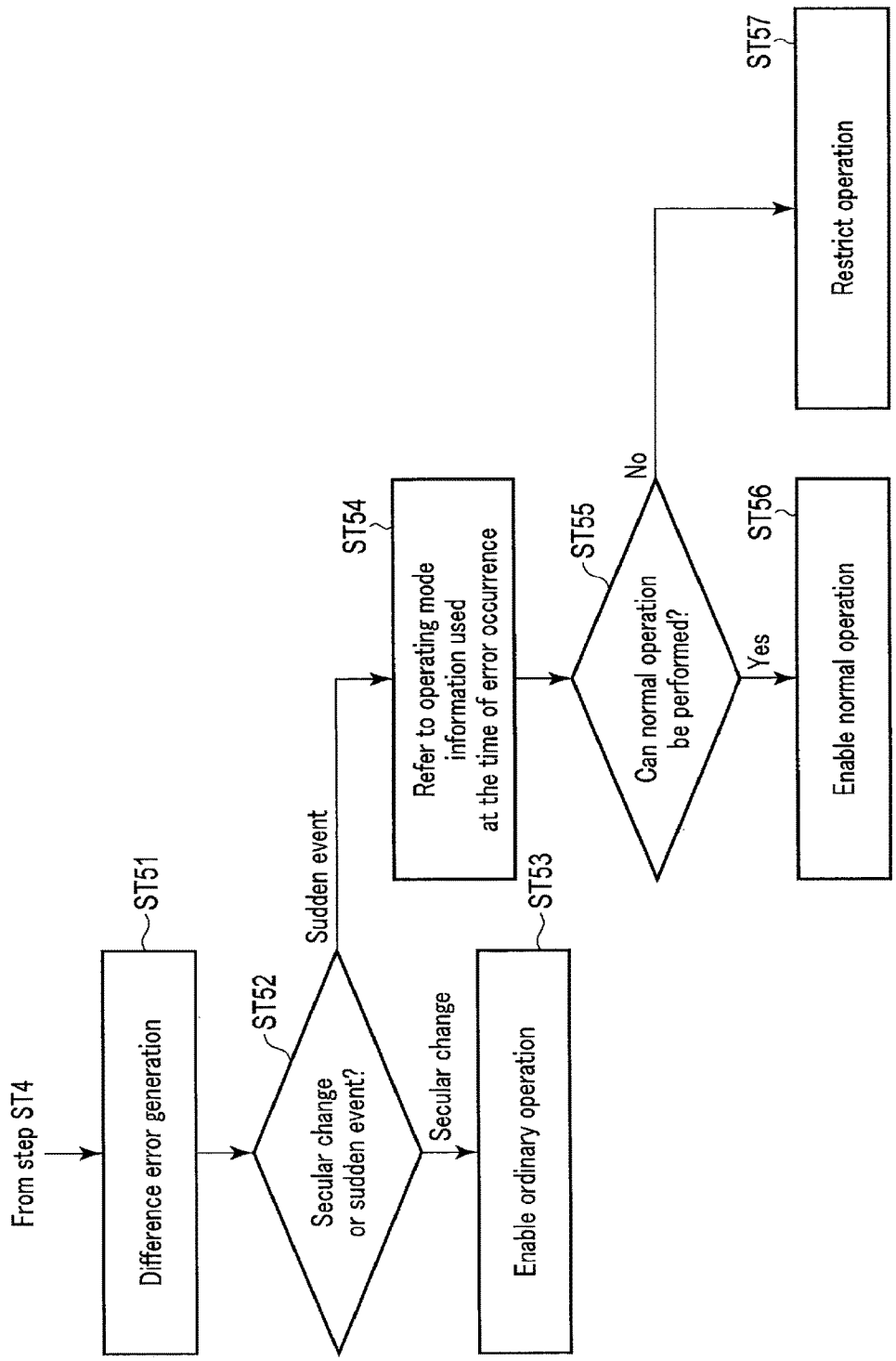
FIG. 14 is a flowchart illustrating an operation performed in the embodiment.

How the medical image diagnostic apparatus having the above configurations operates will be described with reference to the flowchart of FIG. 14.

Let us assume that the determination function 13b of the processing circuitry 13 compares the difference value and the reference value with each other and that a difference error is generated by the difference value exceeding the reference value, as mentioned above (step ST51).

In a similar manner to that described above, the processing circuitry 13 calculates a difference value taken immediately before the reference value is exceeded and a rate of change of the difference value when the reference value is exceeded. Further, the determination function 13b of the processing circuitry 13 determines whether the cause of the exceedance of the reference value is a secular change or a sudden event, based on the calculated rate of change (ST52). The determination result is supplied from the processing circuitry 13 to the system control circuitry 16.

If the determination result indicates a temporal change, the system control circuitry 16 allows the execution of X-ray imaging, and an ordinary operation is enabled (step ST53).

If the determination result in step ST52 indicates a sudden event, the system control circuitry 16 prevents the execution of X-ray imaging. The system control circuitry 16 refers to the operation mode information used at the time of error occurrence (step ST54) and determines whether or not an ordinary operation can be performed (step ST55). Where the operation mode is the manual mode and the operating speed is low (10°/sec), it is determined that the ordinary operation can be performed, and the ordinary operation is enabled (step ST56).

On the other hand, where the operation mode is the auto mode and the operating speed of 3D-DSA imaging is high (50°/sec), it is determined that the ordinary operation cannot be performed, and the operation is restricted (step ST57).

In either case, the fact remains that an error occurs in step ST51, and the necessity for maintenance is indicated on the display 7.

As described above, according to the present embodiment, when the determination result indicates a temporal change, the execution of rotation DSA imaging and 3D-DSA imaging is allowed, and the execution of 3D-LCI imaging which operates with high precision is prevented. Where the determination result indicates a sudden event, the X-ray imaging is prevented. If the determination result indicates a sudden event and if an X-ray image is to be produced by the X-ray imaging after the holding device 8 is rotated, the operation of the driving mechanisms is restricted.

According to the fourth embodiment, therefore, X-ray imaging is prevented, allowed or restricted in accordance with the temporal change, the sudden event, the image quality of the X-ray image produced by the X-ray imaging during the rotation and the X-ray imaging performed after the rotation, and proper control can be performed until the start of the maintenance operation.

To supplement the description, the control parameters such as the accelerating/decelerating time of a rotation axis and the restriction value of motor output are changed in accordance with the situation, and the setting parameters of the control method may be displayed on the UI of the display 7 so that values can be changed automatically or selectively. Accordingly, the operator and the subject are prevented from being harmed by fatal damage to the apparatus, and a third-party harm such as unnecessary exposure to X-rays can be prevented. In addition, since the apparatus is not brought down to a possible degree, the clinical action can be continued without halting the imaging, inspection, etc.

In addition, since the operation, the imaging control, and restrictive operation are performed in accordance with an image-capturing sequence and an operating condition, an uncontrollable situation and the fall of parts can be prevented without halting the image diagnosis and the treatment under fluoroscence. Furthermore, since the irradiation of X-rays is not performed under an operating condition which is unsuitable for imaging or improper for diagnosis, the safety of the subject and the operator is improved, and the apparatus is kept from suffering a fatal damage.

Fifth Embodiment

A medical image diagnostic apparatus according to the fifth embodiment will be described with reference to FIG. 15 and FIG. 16.

The fifth embodiment is a modification of each of the first to fourth embodiments, and a description will be given mainly of how log is displayed and sent to the operator and serviceperson. Unlike the log displayed or sent in the existing technology, log information which is displayed or sent according to the fifth embodiment includes such items as shown in FIG. 16. The "serviceperson" may be called as a "customer engineer."

The medical image diagnostic apparatus 100 is configured such that the processing circuitry 13 can read log information from the storage 12 and display it on the display 7 in response to an operation of the input interface 15 by the operator.

As shown in FIG. 15, the input interface 15 of the medical image diagnostic apparatus 100 is connectable to an external apparatus 20 via a connector. The external apparatus 20 is an information terminal such as a personal computer. In response to an operation by the serviceperson, the external apparatus 20 can access the processing circuitry 13 through the connector and system control circuitry 16, read log information from the storage 12, and display the read log information on the display 21. In response to an operation by the serviceperson, the external apparatus 20 can display an unadjusted difference value of the power transmission mechanism and an adjusted difference value of the power transmission mechanism on the display 21, for each of the operation axes. If an abnormal condition of the power transmission mechanism is detected, the external apparatus 20 may move the related operation axis and enables a difference value to be displayed in real time during the adjustment of the power transmission mechanism. The external apparatus 20 can cause the display 21 to display all items of the log information in response to an operation by the serviceperson.

The medical image diagnostic apparatus 100 is further provided with a communication interface 17 capable of communicating with a remote maintenance system 30 through a network Nw.

The communication interface 17 is circuitry controlled by the processing circuitry 13 and communicates with the external apparatus by wire and/or wireless. The external apparatus is, for example, a remote maintenance system 30.

The remote maintenance system 30 is, for example, InnerVision™ and collects log information on the medical image diagnostic apparatus 100 by way of the network Nw. The remote maintenance system 30 can display the collected log information on a display (not shown). While the log information is displayed, the remote maintenance system 30 can output, based on an operation by the supervisor, a message (e.g., an email message) for sending a serviceperson to the installation site of the medical image diagnostic apparatus 100 and transmit the message to the call center of the apparatus manufacturer or the like. The remote maintenance system 30 only has to be notified of at least an error of the power transmission mechanism, and the difference value of each operation axis does not have to be displayed on the display.

The log information is generated by the processing circuitry 13 and stored in the storage 12, as mentioned above. As shown in FIG. 16, the log information includes "time", "operation event", "operation axis", "normalization values", "difference value of normalization values", "pulse numbers (raw values)", "difference value of pulse numbers", "completion of service adjustment", "down mode", "operation" and "motor output log." The log information may further include an identifier (apparatus ID) that uniquely identifies the medical image diagnostic apparatus 100.

The "time" is temporal information including year, month, day, time, minute and second. The "time" may be referred as "date and time"

The "operation event" is a general term including the operation events of steps ST1-ST9. The "operation event" includes the operation modes mentioned in step ST5.

The "operation axis" is an axis identifier that identifies an axis to be operated. The "operation axis" may be referred to as "electric operating axis." The "operation axis" is not limited to a large operating axis that changes the position of the apparatus during the operation, such as the operating axis of the C arm. For example, the "operation axis" includes a small operating axis that does not change the position of the apparatus during the operation, such as the operating axis of the X-ray collimator. That is, the "operation axis" is intended to cover all operation axes to which the rotation of the driving motor is transmitted through the power transmission mechanism.

The "normalization value of internal encoder" is a value obtained by translating the pulse number (raw value) of the first pulse signal into position information. The "normalization value of load encoder" is a value obtained by translating the pulse number (raw value) of the second pulse signal into position information.

The "difference value of normalization values" is a value representing the difference between the "normalization value of internal encoder" and the "normalization value of load encoder."

The "pulse number (raw value) of internal encoder" is a pulse number (raw value) of the first pulse signal. The "pulse number (raw value) of load encoder" is a pulse number (raw value) of the second pulse signal.

The "difference value of pulse numbers" is a value representing the difference between the "pulse number of internal encoder" and the "pulse number of load encoder."

The "completion of service adjustment" is information indicating that the service adjustment is completed and that the difference value is adjusted.

The "down mode" is information indicating that the down mode is in process.

The "operation" indicates an operation entered from the input interface 15 and covers an operation to start each of the operation events of steps ST1 to ST9. The "operation" includes an operation to execute each of the operation modes of step ST5.

The "motor output log" is a value related to the output of the driving motor or the load. For example, the output torque, current value or voltage value of the driving motor is used as the "motor output log." The output torque, current value and voltage value of the driving motor are measured by a torque meter, an ammeter and a voltmeter (which are not shown), respectively. The value of the "motor output log" tends to increase excessively if the mechanical resistance of the operation axis increases and the operation axis does not move smoothly. Therefore, the value of the "motor output log" is used as an index indicating whether or not the mechanical system of the operation axis is in an abnormal condition.

The log information shown in FIG. 16 is an example and is not limited thereto. That is, the log information is not limited to the items shown in FIG. 16, and the items may be properly changed or new items may be added. With respect to the log information stored in the storage 12, at least part of the items may be displayed, and all items do not have to be displayed.

The other configurations are similar to those of the third embodiment.

Next, a description will be given as to how the medical image diagnostic apparatus having the above configurations displays log information. In what follows, mention will be made of (A) what is displayed on display 7 for the operator, (B) what is displayed on the display of the remote maintenance system 30 for the supervisor, and (C) what is displayed on the display 21 of the external apparatus 20 for the serviceperson. In each of these examples, it is assumed that the medical image diagnostic apparatus 100 generates such log information as shown in FIG. 16 by performing processing similar to that shown in steps ST3-1 to ST3-4 and steps ST8-1 to ST8-2, and stores the generated log information in the storage 12. The display screen in each of these examples may use such a table format as shown in FIG. 16, and log information including desired items may be displayed.

(A) What Is Displayed on Display 7 for Operator

Let us assume that the processing circuitry 13 determines whether the cause of the exceedance of the reference value is a temporal change or a sudden event and causes the display 7 to display the determination result. The system control circuitry 16 restricts the X-ray imaging and the movement or rotation of the holding device 8 in accordance with the determination result.

At this time, the processing circuitry 13 reads log information from the storage 12 and displays the read log information on the display 7 in response to an operation of the input interface by the operator. The displayed log information includes, for example, "operation axis" and "difference value" measured before the power transmission mechanism is adjusted. In addition to the difference value, the processing circuitry 13 may display two pulse numbers (raw values) used for the calculation of the difference value or two normalization values on the display 7. Further, the processing circuitry 13 may display "down mode" and "motor output log" on the display 7. In any case, the log information obtained before the serviceperson makes adjustment is displayed.

(B) What is Displayed on Display of Remote Maintenance System 30 for Supervisor

The processing circuitry 13 displays the determination result regarding the cause of the exceedance of the reference value on the display 7, and in parallel therewith transmits the current log information stored in the storage 12 to the remote maintenance system 30 by way of the communication interface 17 and the network Nw, as described above.

The remote maintenance system 30 displays the transmitted log information on the display. The displayed log information is only required to include at least information indicating that the power transmission mechanism is in an abnormal condition, such as "operation axis", "difference value" and "down mode." The log information does not have to include detailed information such as "pulse number (raw value)", "operation" and "motor output log." While the log information is displayed, the remote maintenance system 30 outputs, based on an operation by the supervisor, a message for sending a serviceperson to the installation site of the medical image diagnostic apparatus 100 and transmit the message to the call center of the apparatus manufacturer or the like. Based on the message, the call center or the like sends a serviceperson to the installation site of the medical image diagnostic apparatus 100. The serviceperson visits the installation site of the medical image diagnostic apparatus 100, carrying the external apparatus 20, and adjusts the power transmission mechanism of the operation axis to eliminate the looseness and backlash. While the power transmission mechanism is being adjusted, the log information is displayed on the display 21 of the external apparatus 20, as will be mentioned in (C) below.

(C) What is Displayed on Display 21 of External Apparatus 20 for Serviceperson

In response to an operation by the serviceperson, the external apparatus 20 accesses the processing circuitry 13 through the connector and system control circuitry 16, reads log information from the storage 12, and displays the read log information on the display 21. For example, in response to the operation by the serviceperson, the external apparatus 20 displays an unadjusted difference value of the power transmission mechanism and an adjusted difference value of the power transmission mechanism on the display 21, for each of the operation axes.

If an abnormal condition of the power transmission mechanism is detected, the external apparatus 20 may move the related operation axis and simultaneously display the difference value in real time during the adjustment of the power transmission mechanism. The operation axis is moved such that the difference value can be obtained. The operations that can be performed for obtaining the difference value include a predetermined operation, a reciprocation movement and any proper operation desired.

In addition to the difference value, the external apparatus 20 can cause the display 21 to display two pulse numbers (raw values) used for the calculation of the difference value or two normalization values. The external apparatus 20 may also cause the display 21 to display not only the difference value, two numbers, two values but also the name of the operation event or the operation mode.

Also, the external apparatus 20 may cause the display 21 to display not only the values of the encoders, the difference value and the name of the operation mode but also values related to the output and load of the driving motor. For example, with respect to a target operation axis, the torque of the driving motor and the difference value of the pulse numbers (raw values) can be associated with each other and displayed.

Furthermore, the external apparatus 20 can cause the display 21 to display desired items of the log information in response to an operation by the serviceperson.

As described above, according to the present embodiment, necessary information of the log information can be displayed on the display 7 of the medical image diagnostic apparatus 100, the display of the remote maintenance system 30 or the display 21 of the external apparatus 20, in accordance with an operation performed by the operator, supervisor or serviceperson.

According to at least one of the embodiments described above, the holding device 8 is rotated by transmitting the rotation of the driving motor to the rotation axes by means of the power transmission mechanism. The first encoder detects the rotation of the driving motor. The second encoder detects the rotation of the rotation axis. An abnormal state of the power transmission mechanism is detected based on the time difference between a first pulse of the first pulse signal output from the first encoder and a corresponding second pulse of the second pulse signal output from the second encoder.

Accordingly, since the need for a visual check, which was performed regularly in the past, can be eliminated, the low operation rate caused by the regular check can be prevented.

The term "processor" used in the above descriptions is, for example, a central processing unit (CPU) or a graphics processing unit (GPU), or may include the following types of circuitry: an application-specific integrated circuitry (ASIC), a programmable logic device (such as a simple programmable logic device (SPLD), or a complex programmable logic device (CPLD), a field programmable gate array (EPGA) or the like. The processor reads the programs stored in the storage and executes them to realize the respective functions. The programs may be incorporated in the circuitry of the processor, instead of storing them in the storage. In this case, the processor reads the programs incorporated in its circuitry and executes them to realize the respective functions. The processors described in connection with the present embodiment are not limited to single-circuit processors. A plurality of independent processors may be combined and integrated as one processor having multiple functions. Furthermore, a plurality of structural elements shown in FIG. 1 may be integrated as one processor having multiple functions.

The holding unit 81 and the holding unit holder 32 described in connection with one embodiment are examples of the holding device recited in the claims. The holding unit holder rotation mechanism described in connection with one embodiment is an example of the driving unit recited in the claims. The first measurement circuitry 11a described in connection with one embodiment is an example of the processing circuitry recited in the claims. The storage 12, the log function 13a and processing circuitry 13 described in connection with one embodiment is an example of the processing circuitry and the memory recited in the claims. The determination function 13b, output function 13c and processing circuitry described in connection with one embodiment is an example of the processing circuitry recited in the claims. The system control circuitry 16 described in connection with one embodiment are example of the control circuitry recited in the claims. The second measurement circuitry 11b described in connection with one embodiment is an example of the processing circuitry recited in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
 a holding device configured to hold an X-ray generator and an X-ray detector such that the X-ray generator and the X-ray detector are rotatable around a rotation axis;
 a driving unit including a driving motor and a power transmission mechanism and configured to transmit a rotating force of the driving motor to the rotation axis through the power transmission mechanism so as to rotate the holding device;
 a first encoder configured to detect a rotation of the driving motor;
 a second encoder configured to detect a rotation of the rotation axis; and
 processing circuitry configured to detect an abnormal state of the power transmission mechanism, based on a time difference between a first pulse of a first pulse signal output from the first encoder and a corresponding second pulse of a second pulse signal output from the second encoder.

2. The medical image diagnostic apparatus according to claim 1, wherein the first pulse is a leading pulse of the first pulse signal, and
 the second pulse is a leading pulse of the second pulse signal.

3. The medical image diagnostic apparatus according to claim 2, wherein the processing circuitry stores a history of a difference value representing the time difference in a memory, if the difference value exceeds a reference value, determines whether the cause of exceedance of the reference value is a temporal change or a sudden event, based on how the time difference is before the reference value is exceeded and how the difference value changes after the reference value is exceeded, and outputs a determination result.

4. The medical image diagnostic apparatus according to claim 3, further comprising control circuitry configured to allow execution of X-ray imaging if the determination result indicates a temporal change and an X-ray image to be produced by the X-ray imaging performed during rotation of the holding device is high in image quality, and prevent execution of the X-ray imaging if the X-ray image is low in image quality.

5. The medical image diagnostic apparatus according to claim 4, wherein the control circuitry prevents the X-ray imaging if the determination result indicates a sudden event.

6. The medical image diagnostic apparatus according to claim 3, further comprising control circuitry configured to restrict an operation of the driving unit if the determination result indicates a sudden event and an X-ray image is to be produced by the X-ray imaging performed after rotation of the holding device.

7. The medical image diagnostic apparatus according to claim 6, wherein the processing circuitry makes a determination in an auto mode in which the X-ray imaging is executed in accordance with a predetermined image-capturing sequence or in a manual mode in which processing is performed in response to an operation by an operator,
the control circuitry switches either the auto mode or the manual mode to a down mode and restricts the operation in the down mode, and
the down mode is a mode in which an operation of a rotation axis whose difference value exceeds the reference value is stopped and an operation of another rotation axis is enabled.

8. The medical image diagnostic apparatus according to claim 1, wherein the processing circuitry stores a history of a difference value representing the time difference in a memory, if the difference value exceeds a reference value, determines whether the cause of exceedance of the reference value is a temporal change or a sudden event, based on how the time difference is before the reference value is exceeded and how the difference value changes after the reference value is exceeded, and outputs a determination result.

9. The medical image diagnostic apparatus according to claim 8, further comprising control circuitry configured to allow execution of X-ray imaging if the determination result indicates a temporal change and an X-ray image to be produced by the X-ray imaging performed during rotation of the holding device is high in image quality, and prevent execution of the X-ray imaging if the X-ray image is low in image quality.

10. The medical image diagnostic apparatus according to claim 9, wherein the control circuitry prevents the X-ray imaging if the determination result indicates a sudden event.

11. The medical image diagnostic apparatus according to claim 8, further comprising control circuitry configured to restrict an operation of the driving unit if the determination result indicates a sudden event and an X-ray image is to be produced by the X-ray imaging performed after rotation of the holding device.

12. The medical image diagnostic apparatus according to claim 11, wherein the processing circuitry makes a determination in an auto mode in which the X-ray imaging is executed in accordance with a predetermined image-capturing sequence or in a manual mode in which processing is performed in response to an operation by an operator,
the control circuitry switches either the auto mode or the manual mode to a down mode and restricts the operation in the down mode, and
the down mode is a mode in which an operation of a rotation axis whose difference value exceeds the reference value is stopped and an operation of another rotation axis is enabled.

13. The medical image diagnostic apparatus according to claim 8, further comprising control circuitry configured to prevent X-ray imaging from being performed during rotation of the holding device if the determination result indicates a sudden event.

14. The medical image diagnostic apparatus according to claim 3, further comprising control circuitry configured to prevent X-ray imaging from being performed during rotation of the holding device if the determination result indicates a sudden event.

15. A medical image diagnosis apparatus comprising:
a holding device configured to hold an X-ray generator and an X-ray detector such that the X-ray generator and the X-ray detector are rotatable around a rotation axis;
a driving unit including a driving motor and a power transmission mechanism and configured to transmit a rotating force of the driving motor to the rotation axis through the power transmission mechanism so as to rotate the holding device;
a first encoder configured to detection a rotation of the driving motor;
a second encoder configured to detect a rotation of the rotation axis; and
processing circuitry configured to translate a pulse number of a first pulse signal output from the first encoder into a pulse number of a second pulse signal output from the second encoder, thereby obtaining a translation pulse number, to correct the translation pulse number such that a corrected translation pulse number does not include a pulse number resulting from a slight rotation which the holding device makes due to a gravitation direction in accordance with a rotation start angle and a rotation end angle, and to measure a difference value between the corrected translation pulse number and the pulse number of the second pulse signal output from the second encoder, as a value corresponding to a backlash of the power transmission mechanism.

16. The medical image diagnostic apparatus according to claim 15, wherein the processing circuitry stores a history of the difference value in a memory, if the difference value exceeds a reference value, determines whether a cause of exceedance of the reference value is a temporal change or a sudden event, based on how the difference value is before the reference value in the memory is exceeded and how the difference value changes after the reference value is exceeded, and outputs a determination result.

17. The medical image diagnostic apparatus according to claim 16, further comprising control circuitry configured to allow execution of X-ray imaging if the determination result indicates a temporal change and an X-ray image to be produced by the X-ray imaging performed during rotation of the holding device is high in image quality, and prevent execution of the X-ray imaging if the X-ray image is low in image quality.

* * * * *